(12) United States Patent
Yen

(10) Patent No.: US 9,114,127 B2
(45) Date of Patent: Aug. 25, 2015

(54) BIOLOGIC DEVICES FOR HEMOSTASIS

(76) Inventor: Richard C. K. Yen, Yorba Linda, CA (US)

( * ) Notice: Subject to any disclaimer, the term of this patent is extended or adjusted under 35 U.S.C. 154(b) by 1342 days.

(21) Appl. No.: 12/148,713

(22) Filed: Apr. 22, 2008

(65) Prior Publication Data

US 2009/0304804 A1 Dec. 10, 2009

Related U.S. Application Data

(60) Provisional application No. 60/930,248, filed on May 15, 2007.

(51) Int. Cl.
*A61K 38/36* (2006.01)
*A61K 9/16* (2006.01)
*A61K 38/48* (2006.01)

(52) U.S. Cl.
CPC ............... *A61K 38/36* (2013.01); *A61K 9/1658* (2013.01); *A61K 38/363* (2013.01); *A61K 38/4846* (2013.01)

(58) Field of Classification Search
None
See application file for complete search history.

(56) References Cited

U.S. PATENT DOCUMENTS

| 5,725,804 A | 3/1998 | Yen |
| 2002/0142046 A1 * | 10/2002 | Yen ............................. 424/491 |
| 2008/0064628 A1 * | 3/2008 | Goodall et al. .................. 514/8 |

* cited by examiner

*Primary Examiner* — Anand Desai
(74) *Attorney, Agent, or Firm* — David A. Guerra

(57) ABSTRACT

A microscopic protein device and the method of manufacture and the use of such a device for hemostasis. The device, made with biologic material such as serum albumin from a human or animal source, is less than five micron in any one dimension and typically less than one micron in diameter. It does not have any other biological or drug molecules attached to it in vitro. However, the device has properties that allow it to capture, concentrate, carry or bind biomodifying molecules, such as coagulation factor(s), or potentially other drugs, after exposure to plasma in vitro; and possibly in vivo as well. After infusion of said device intravenously inside the body, hemostatic effects can be demonstrated.

7 Claims, No Drawings

BIOLOGIC DEVICES FOR HEMOSTASIS

CROSS-REFERENCE TO RELATED APPLICATIONS

This application claims the benefit of priority of U.S. Provisional Application No. 60/930,248 filed on May 15, 2007. The entire disclosures of the prior applications are incorporated herein by reference.

BACKGROUND OF THE INVENTION

1. Field of the Invention

The present invention relates to the field of microscopic particulate devices made of biologic material suitable for intravenous administration, their methods of production and the use of such devices inside the body to treat medical conditions. More specifically, the present invention relates to the field of protein particles smaller than five micron in any one dimension, which are inert by themselves but serve as devices to capture or concentrate or carry biological, or drug molecules already in the blood, such that a combination of the device with captured biological or drug molecule can have unexpected or enhanced medicinal value.

One particular application is in the field of hemostasis, where after intravenous infusion, the device may capture molecules inside the body, such as a single component or a variety of coagulation factors, which then render the combination of device plus biological molecule capable of decreasing blood loss or shortening (improving) bleeding time. The mechanism of capture of endogenous molecules is unknown, nor is the exact mechanism of medicinal benefit.

These devices are expected to greatly benefit patients with insufficient platelet concentrations or diminished platelet function, or in patients with tendencies of bleeding due to other causes. Patients that are expected to benefit included thrombocytopenic patients from dilutional thrombocytopenia, cancer, thrombocytopenia from cancer treatments, idiopathic thrombocytopenia purpura, aplastic anemia, transplant patients, anticoagulant overdose, antiplatelet medication overdose and hemorrhagic episodes such as from Ebola or Dengue fever outbreaks. These devices can potentially be used for treatment as well as prophylactic use such as in surgical patients where perioperative blood loss is expected to be extensive but erythrocyte or platelet transfusion services are lacking; or in battlefield conditions where transfusion services are difficult.

2. Description of the Prior Art

Conventional methods of drug administration include oral, intravenous, intramuscular, subcutaneous, intraperitoneal, inhalation routes, nasal and mucosal applications. Numerous authors, including Yen had disclosed method of production and products where drugs can be encapsulated on the surface or interior of protein spheres for the purpose of targeted delivery to specific organs or sites to decrease systemic toxicity of the drug and/or enhance effectiveness at the site of action, particularly after intravenous infusion.

In the U.S. Pat. No. 5,069,936 ("Manufacturing Protein Microspheres") Yen disclosed a method of producing albumin spheres by two methods (Column 4, line 53 to Column 5, line 28.) Both methods emphasized the importance of adding a surfactant or detergent to the protein solution before the formation of spheres from the protein solutions. One method ("Pre-link" method) used a cross-linking agent in a concentration sufficient to mildly cross-link protein molecules in a solution without the formation of a gel, before the addition of a desolubilizing or desolvation agent (such as ethanol) to form spheres. This concentration of crosslinking agent was, however, capable of binding the protein molecules together irreversibly in the form of spheres, even if the desolvation agent was subsequently diluted or removed. Another method ("Post-link" method) formed (reversible or resolubilizable) spheres first by the addition of a desolubilizating agent to a solution of protein. This step needs to be followed by the addition of a cross-linking agent in a concentration sufficient to stabilize the spheres against resolubilization during further processing (when the desolvation agent would be diluted or removed.)

U.S. Pat. No. 5,069,936 not only disclosed how to manufacture protein spheres but also taught that the spheres produced by either disclosed method can be used to bind other biological or drug molecules by covalent-bonding the drug to the spheres via a crosslinking agent (e.g. IgG, Example 7, Column 29) before administration to the patient. This was essentially achieved by adding an additional amount of crossing linking molecules (such as glutaraldehyde) after the spheres had been formed and irreversibly stabilized against resolubilization. This additional step of adding a crosslinking agent was intended to bind additional molecules to the spheres and not for the formation or stabilization of the spheres themselves. The biological activity of such spheres covalently bonded with biological or drug molecules (internally or on the surface of the spheres) entirely comes from the bound biological or drug molecules. In fact, control "blank" spheres (i.e. protein microspheres with no biomodifying agents, Example 9, Column 31) had been shown to demonstrate no efficacy as compared to a soluble drug such as adriamycin, or the same drug (adriamycin) encapsulated within the spheres.

The present invention described a series of novel methods to produce protein spheres without the need of adding or including surfactants or detergents to the protein solution before the formation of spheres. The sphere suspensions produced contained monodispersed spheres without aggregates and without large spheres (larger than 5 micron in diameter) that can clog capillaries when infused intravenously to patients.

Another advantage of the product made with the present invention is their small size. Because the spheres can be made with the present invention to be smaller than 1 micron in diameter, they tend to remain in suspension without sedimentation during prolong storage. Therefore, there is no need to lyophilize the suspension which was necessary with the preparations made with the disclosed methods in the prior art. Even with the expensive step of lyophilization with products made with the prior art, upon reconstitution of the lyophilized power with a fluid, the large spheres produced by the prior art can still sediment from the suspension and form a cake after some time.

Another property of the spheres manufactured with the series of novel methods disclosed in this invention is their efficacy in treating bleeding from thrombocytopenia. It is totally unexpected that upon certain changes in the method of production to be described in this application, that control or "blank" spheres, after intravenous infusion into thrombocytopenic animals, demonstrated hemostatic efficacy. These spheres did not have any fibrinogen or other coagulation (or other drugs) bound to them during the synthesis procedure. And spheres produced by this novel method after being kept at room temperature as a suspension for prolong periods of time were still efficacious.

The mechanism of shortening the bleeding time of thrombocytopenic animals by these novel "blank" spheres or microscopic devices made with the present invention is unknown. One can theoretically postulate a number of mechanisms, including the ability of these novel devices to bind biological molecules in vivo, such as any number of coagulation factors in any number of combinations. The potential binding of such molecules occurs after the infusion of such devices into the body. Since the exact identity and the concentration of biological molecules that hypothetically bind spontaneously to the spheres are difficult to ascertain and the molecules come from the blood in circulation and not added in vitro outside the body, such spheres essentially serve as devices. The devices apparently have the proper properties to capture, or concentrate, or carry the appropriate biological molecules to bring about the clinical efficacy. The device, however, without the appropriate additional molecules introduced in vivo is not expected to have by itself any medicinal efficacy.

It is further emphasized that the mechanism of this hypothetical combination of device with effective molecules (called "activated devices" from hereon) is also unknown, but can take the form of targeting the device to a wound site, or enhancement of endogenous platelet function (in a thrombocytopenic condition or in a patient with normal platelet concentration), or any number of unknown mechanisms.

In another patent, U.S. Pat. No. 6,264,988 B1 ("Fibrinogen-coated Microspheres") Yen disclosed products and methods of production where fibrinogen molecules are attached to stabilized albumin spheres. Again, the spheres were made with added surfactant or detergent in the protein solution before the addition of a desolvation agent. However, the disclosed methods of production resulted in suspensions of spheres with a minority population of spheres which are too large in size. The patent described the use of filtration or centrifugation to remove "large particles" (larger than 7 micron in diameter, column 8, which will obstruct blood capillaries) before or after the addition of fibrinogen molecules to the spheres. The spheres produced by the present invention, by contrast, are all smaller than 5 micron and therefore the suspension requires no filtration or centrifugation steps. In particular, and of great relevance to the present invention is the disclosure in U.S. Pat. No. 6,264,988 B1 the lack of efficacy of "control spheres" (CS) which are albumin spheres without added fibrinogen, made by said disclosed methods. CS showed (as expected) no in vivo activity in the correction of bleeding time (FIG. 6) or the amount of blood loss (FIG. 7B) among thrombocytopenic rabbits. In vitro studies using ADP to aggregate mixtures of CS with human platelets showed non-participation of CS while human platelets form pure platelet aggregates (FIG. 14B.)

Therefore it is totally unexpected and novel that the presently disclosed new method of production of protein spheres without the addition in vitro of a biomodifying molecule such as fibrinogen or other clotting factor(s) can result in a product which has in vivo biological and medicinal efficacy.

Attempts to study the mechanism of such efficacy is expected not to be fruitful for several reasons: (1) It would be difficult to recover infused protein particles from the circulation compartment of the infused subject; which contains small particles such as platelet fragments, endothelial cell debris and other protein aggregates; (2) Any recovered particles are only a fraction of the infused population of particles. It is well known that rheologically smaller particles flow near the wall of capillaries and blood vessels, while larger particles flow near the centre of the blood vessels. Any studies performed on recovered particles only revealed the property of the recovered population of particles, probably collected from near the center of the circulatory compartment and not the original population of devices; (3) The biomodifying molecule is derived from the blood compartment in vivo which becomes attached to the device in vivo. It may detach from the particle after isolation, particularly in purification steps designed to remove soluble plasma proteins and other blood elements, e.g. red cells and platelets.

However, in vitro studies can offer some insights as to what these particulate devices can bind when mixed with plasma or fibrinogen solutions in vitro. These will be discussed as each experiment is described in the following sections.

In another patent (U.S. Pat. No. 5,725,804 "Non-Crosslinked Protein Particles for Therapeutic and Diagnostic Use") Yen described a method of making spheres that will not redissolve upon removal or dilution of the desolvation agent. The mechanism of stabilization is unknown but can be achieved by the addition of a number of unrelated chemicals and drugs, all of which are not crosslinking agents. This prior art provides no motivation for anyone skilled in the art to use a crosslinking agents in the manner with which those non-crosslinking agents were used because the specific purpose of that patent was to teach how non-crosslinking agents could stabilize spheres without the presence or addition of crosslinking agents in any of the production steps. It is therefore unexpected and novel and non-obvious that the series of methods to be described here can produce sphere suspensions in the absence of added surfactants or detergent in the protein solution, and result with crosslinked spheres possessing desirable properties and medicinal efficacy.

In an abstract, published in the Journal of Thrombosis and Haemostasis, vol 5, supp 1, August, 2007, Appleby et al. described the design of a "platelet substitute" using human albumin microparticles to bind the fibrinogen-binding peptide Gly-Pro-Arg-Pro (GPRP). So, in stead of binding fibrinogen directly onto their microparticles, these investigators bound an intermediate peptide (GPRP) onto the microparticles. Their approach of binding fibrinogen indirectly onto their microparticles is obviously non-novel. Published data had shown that a link between a particle (such as a red cell) and a fragment from the fibrinogen molecule can facilitate the attachment of the particle (called "thromboerythrocyte") to platelets. (see "Thromboerythrocytes" by Coller B S, et al, in J. Clin. Invest 1992, 89:546-555.) In contrast, data to be presented below for this invention showed that no intermediate molecules are needed on the spheres made with this invention, in order to bind fibrinogen onto the sphere either in vitro or in vivo.

BRIEF SUMMARY OF THE VARIOUS NOVEL METHODS

All of the following methods do not have added surfactant or detergent in the protein solution before the addition of a desolvation agent to form spheres. Some of the names may be similar to those described in the Prior Art, but the products made with these novel methods are different from those produced in the Prior Art. The name can refer to the method of production or the product produced by the method.

1. "Pre-link" means the crosslinking agent is added to the protein solution before the desolvation agent is added. In this method the crosslinking agent binds on sites on the protein molecules which are surrounded by water molecules with the protein molecule folded in the most natural state. Then at the addition of the desolvation agent, the protein molecules with attached crosslinking agents come together to form spheres.
2. "Mid-link" means the crosslinking agent is first pre-mixed with the desolvation agent; and then the mixture is added to the protein solution. In this case the time of interaction of protein molecules with the crosslinking agent is of the same duration as that with the desolvation agent. In this method, the crosslinking molecules attach to some individual protein molecules in solution (surrounded by water of hydration) as well as those that have other protein molecules as their near-neighbors (partially surrounded by water of hydration.) Since the spheres are in the process of formation under the simultaneous action of the desolvation agent and the premixed crosslinking agent, it is conceivable that some protein molecules already have crosslinking agents attached (completely or partially) as they come together and some not yet. It is also conceivable that additional crosslinking molecules will bind to the sphere after it is essentially formed. Since having another protein molecules as a near-neighbor (instead of water of hydration) may change the conformation of a protein molecule, the site of binding for the crosslinking agent may be different from those protein sites bound by the crosslinking agent under the "Pre-link" method mentioned above, or other methods to be mentioned below.

3. "Post-link" means the crosslinking agent is added after the desovation agent had been added to the protein solution to form spheres. In this case the crosslinking agent is added to a turbid suspension of spheres which otherwise can redissolve if the desolvation agent is diluted or removed. In this case, the crosslinking molecule will bind onto sites on the protein molecules which have already been assembled as a sphere. The site of binding by the crosslinking agent may be different from those protein sites available for binding by the crosslinking agent when-used under the "Pre-link" or "Mid-link" method mentioned above, or under other methods to be mentioned below.

4. "Bi-link" means the crosslinking agent is added in two separate steps. The first step involves adding a low concentration of crosslinking agent to the protein solution for a short time. This sub-stabilizing concentration of crosslinking agent is not sufficient to prevent resolubilization of the spheres upon dilution or removal of the desolvation agent but has the beneficial effect of preventing formation of a minority population of spheres larger than the great majority of the spheres in the suspension. Then the desolvation agent will be added, followed by a second step of adding a stabilizing concentration of crosslinking agent which will prevent the spheres from resolubilization upon removal or dilution of the desolvation agent. Again the site on the protein molecules available for binding by the crosslinking agent before the formation of the sphere and after the formation of the sphere may be different from all the other methods mentioned in this section.

5. "BiMid-link" means the crossing linking agent is added in two separate steps. The first step, like the Bi-link method, involves the addition of a low sub-stabilizing concentration of crosslinking agent to the protein solution for a short time. The second step involved the addition of a stabilizing concentration of crosslinking agent which had been premixed with the desolvation agent. The advantage of this method is that the spheres formed do not have any detectable minority population of spheres of unusual size compared to the great majority of spheres formed and there is one fewer step of addition or mixing compared to the Bi-link method. Since the crosslinking agent had been pre-mixed with the desolvation agent, the mixture was added in one step to the protein solution (pre-treated with the sub-stabilizing concentration of crosslinking agent) to form spheres. As discussed above, the site of binding by the crosslinking molecules on the protein molecules may be different from those produced by the other methods mentioned in this section.

SUMMARY OF THE INVENTION

This invention discloses a novel microscopic protein device and the method of manufacture and the use of such a device for hemostasis. The device, made with biologic material such as serum albumin from a human or animal source, is less than five micron in any one dimension and typically less than one micron in diameter. It does not have any other biological or drug molecules attached to it in vitro. However, the device has properties that allow it to capture, concentrate, carry or bind biomodifying molecules, such as coagulation factor(s), or potentially other drugs, after exposure to plasma in vitro; and possibly in vivo as well. After infusion of said device intravenously inside the body, hemostatic effects can be demonstrated. Thrombocytopenic animals infused with said protein device showed improved bleeding time and less blood loss from surgical wounds. It is expected that animals with normal platelet count after infusion of said protein device will also have less blood loss or bleeding tendencies when challenged. The mechanism of the suggested binding of biomodifying molecules is unknown, nor is the mechanism of medicinal benefit.

BRIEF DESCRIPTIONS OF THE DISCOVERIES IN THIS PATENT

It was discovered, according to this disclosure and described in Experiment One that human serum albumin solutions purchased from various vendors were different in the composition of the excipient fluid and did not result in similar sphere suspensions using the same production method. In particular, it was found that novel methods of synthesis, not requiring the addition of surfactants could result in suspensions which did not have spheres larger than 5 microns in diameter, nor the presence of aggregates.

It was discovered, according to this disclosure and described in Experiment Two that a new method of synthesis of protein spheres was highly effective. The method was called Mid-link because the crosslinking agent was premixed with the desolvation agent. The mixture was then added to a protein solution in the absence of additional surfactants or detergents to form useful sphere suspensions.

It was discovered, according to this disclosure and described in Experiment Three that further refinement of the Mid-link method could produce suspensions without spheres larger than 5 micron in diameter. This allows productions of spheres without the need to filter out or remove large spheres capable of clogging blood vessels, as produced by methods of prior art.

It was discovered, according to this disclosure and described in Experiment Four, that spheres produced by the novel Post-link and Mid-link method, both of which did not require the presence of added surfactant to the protein solution, could bind fibrinogen in vitro.

It was discovered, according to this disclosure and described in Experiment Five, that another novel method of production of spheres, by dividing the addition of crosslinking agent into two separate steps, had the surprising effect of reducing the formation of large spheres or particles during synthesis of the suspension. The first step involved using a concentration of crosslinking agent that by itself was insufficient to prevent the resolubilization of sphere upon dilution of the desolvation agent. The second step involved addition of a concentration of crosslinking agent to the turbid suspension for the purpose of irreversibly stabilizing spheres from dissolving again. The method is called the Bi-link method.

It was discovered, according to this disclosure and described in Experiment Six, that Pre-link sphere when exposed to plasma in vitro could spontaneously bind more than one coagulation factors without the addition of crosslinking agents.

It was discovered, according to this disclosure and described in Experiment Seven, that the novel Bi-link method can result in spheres that can bind fibrinogen.

It was discovered, according to this disclosure and described in Experiment Eight, that Bi-link spheres which had been coated with fibrinogen in vitro and those not coated with fibrinogen in vitro were both efficacious in the improvement of bleeding time in thrombocytopenic rabbits. This is a most un-expected result since control Post-link spheres prepared by prior art using a method involving added surfactant in the protein solution but having no fibrinogen added in vitro had repeatedly demonstrated no medicinal benefit in thrombocytopenic rabbits.

It was discovered, according to this disclosure and described in Experiment Nine, that both blank Pre-link and blank Bi-link spheres (i.e. spheres with no added fibrinogen in vitro) were effective in improvement of the bleeding time of thrombocytopenic rabbits.

It was discovered, according to this disclosure and described in Experiment Ten that spheres could be subjected to extreme hydrostatic pressure as a means of terminal sterilization. The process did not damage the suspension which remained effective in the treatment of thrombocytopenic rabbits.

It was discovered, according to this disclosure and described in Experiment Eleven, that by using dialyzed human serum albumin which had lower salt contents, a high concentration of spheres could be obtained in the suspension.

It was discovered, according to this disclosure and described in Experiment Twelve, that the spheres prepared from dialyzed human serum albumin using the present novel method of synthesis were monodisperse in size distribution and were different from those described in the prior art.

It was discovered, according to this disclosure and described in Experiment Thirteen, that spheres prepared by the novel Mid-link method when exposed to a low concentration of fibrinogen in plasma, were capable of capturing, concentrating and binding the fibrinogen molecules from the plasma, thus providing insight into why blank spheres were capable to serve as devices in the treatment of thrombocytopenic rabbits.

It was discovered, according to this disclosure and described in Experiment Fourteen, that Mid-link method could be adapted easily toward a mass production method and the resultant spheres could be terminally sterilized by heating to 60 degree Centigrade for 10 hours while maintaining efficacy in improving the bleeding time of thrombocytopenic rabbits.

It was discovered, according to this disclosure and described in Experiment Fifteen, that the novel BiMid-link method could produce spheres very uniform in size with essentially no minority population of spheres of unusually large sizes. The spheres could be produced in vitro with or without coating with fibrinogen. It was discovered that both types of spheres produced by this method were effective in the treatment of bleeding in thrombocytopenic animals.

It was discovered, according to this disclosure that a new method of treatment of bleeding from thrombocytopenia or platelet dysfunction can be achieved by infusion of a microscopic biologic device which did not have fibrinogen added in vitro during the manufacturing procedures as made in accordance with the present invention.

It was discovered, according to this disclosure that a new method of treatment of bleeding from thrombocytopenia or platelet dysfunction can be achieved by infusion of a microscopic biologic sphere which had fibrinogen added in vitro during the manufacturing procedures as made in accordance with the present invention.

DETAILED DESCRIPTION OF THE INVENTION

Patients (human and animals) can bleed due to a variety of reasons. One reason is external injury such as from trauma, or during a surgical operation. Dilutional thrombocytopenia, a condition of bleeding as a result of replacing only red blood cells without the infusion of platelets after major loss of whole blood, is a very common cause of perioperative bleeding.

Another reason for bleeding is due to internal derangements in the clotting system which can be the result of genetic defectives, or viral infections, or medication. This will lead to prolong periods of bleeding or excessive volume of blood loss in internal organs.

The clotting mechanism consists of mainly two systems, which work in a cooperative way. The commonly known is the soluble system, comprising mainly of the clotting factors. The less well-known system involves the platelets, which are very small but still visible particles in the blood, typically ranging from 7.4 to 10.4 famtoliters (or cubic micrometer) in volume. This invention mainly deals with the manufacture and use of small spheres which can mimic the function of platelets and therefore may be regarded in some ways as "artificial platelets."

The clotting factors are protein molecules dissolved in the blood which will become activated around a wound site and which (by a cascading or amplifying system) will form an insoluble "fibrin clot" to "plug" the wound site. However, it takes some time for this kind of soluble system to form a stable insoluble clot, with this system alone. A faster system is the platelet system, which when activated around a wound site, can convert an inert platelet (which is already a small particle) to an activated platelet within fractions of a second. The major biochemical event of platelet activation is the binding of a coagulation factor, specifically that of fibrinogen (factor I), onto the surface of platelets. The speed with which platelet-bound fibrinogen can convert to fibrin on the surface of an activated platelet is much faster than the speed of soluble fibrinogen in the blood (not bound to platelets) to convert to fibrin. Therefore, the two systems, though separate, work together to form clots efficiently around a wound site. There are of course many other important functions performed by activated platelets, which one skilled with the detail knowledge of platelets will appreciate.

The concentration of platelets is very important. In healthy human patients, the normal range of platelet is 130 to 400 thousand platelets per microliter of blood. Patients (human or animals) suffering from an insufficient concentration of platelets will have prolong "bleeding time" (the time taken for a wound to stop bleeding spontaneously, e.g. without application of external pressure) and "bleeding volume" (the volume of blood loss during the bleeding period.) Thrombocytopenia is the medical term to describe the condition of a patient not having a sufficient concentration of platelet. This condition can be caused by cancer, which is damaging the platelet production ability of the bone marrow, or from cancer treatment.

The reason why thrombocytopenic patients have prolong bleeding time is often ascribed to the inability of activated platelets to reach each other (due to the low concentration) to physically link up to eventually form the platelet plug. An artificial platelet product that can in some way fill the void and provide a means to link up activated platelets or form co-aggregates with activated platelets during the process of the formation of a platelet plug will therefore be very important for the medical and surgical patient. One approach to the formation of an artificial platelet is the binding of fibrinogen onto the surface of a compatible protein sphere that the body may be "fooled" into regarding as a platelet: The fibrinogen molecules can be added to the spheres in vitro during the manufacturing step, or added to the sphere in vivo, after administration of "blank" spheres to the patient. Other mechanism of action by artificial platelets, such as stimulation of any endogenous platelet function among the low concentration of platelets, or any other mechanism apparent to those skilled in the biochemistry of the clotting system, are of course possible.

Sometime patients are given anti-platelet medication to prevent the formation of platelet plugs, such as in patients with a history of stroke or heart attack. Aspirin and other newer antiplatelet medications such as Aggrastat (tirofiban), Agrylin (anagrelide), Integrilin (eptifibatide), Persantine (dipyridamole), Plavix (clopidogrel), Pletal (cilostazol), ReoPro (abciximab), Ticlid (ticlopidine), Ventavis (iloprost) are some examples. These medications typically do not affect the platelet concentration (or platelet count) but affect platelet function. The patient can be called thrombocytopathic. However, since a body with a normal platelet-producing capacity continuously produces functional platelets from the bone marrow, some physicians consider such anti-platelet medication-induced thrombocytopathic state as "functional thrombocytopenia": the small concentration of newly produced and not affected platelets still can function but not in sufficient numbers. An artificial platelet product can therefore function under these conditions too.

Occasionally a patient on anti-platelet medication may have an overdose, or the patient may need an emergency operation. At present there are no ready reversal agents for anti-platelet medication. An artificial platelet product can be infused to remedy the functional thrombocytopenia.

It is expected that an artificial platelet product such as this invention will improve the hemostatic condition of patients when given as a prophylactic treatment for patients who are not yet thrombocytopenic, nor thrombocytopathic, but are expected to need platelet transfusion soon, because of expected large blood loss during a surgical procedure or facing any dangerous conditions that will lead to massive bleeding. In some situations platelets are not available and therefore the artificial platelet product will be an ideal substitute.

This invention describes a biologic device, its method of manufacture and its use in human and animal patients. The device is made of biologic material to which no surfactant or detergent has been added, such as protein molecules; more specifically serum albumin, of human or animal origin. The device is suitable for administration to a patient. The biologic device initially has no active molecule bound to it, but the biologic device has the capacity to directly capture at least one other biologically active molecule, such as a drug, or a soluble coagulation factor. The capture of at least one biologically active molecule can occur in vitro or in vivo.

Although previous publications showed that the addition of a surfactant or detergent to the albumin solution is important during the manufacturing process to prevent formation of aggregates, this invention discovered that no surfactant or detergent needed to be added to the protein solution, such as an albumin solution, to produce useful suspensions of spheres without aggregates, according to the present invention.

Of particular interest is that "blank" spheres, defined as spheres not having any "biologically active molecule" or biomodifying molecule added to the albumin spheres during the manufacturing process (or "in vitro") can have a medicinal effect after administration to a patient. Biomodifying molecules are those molecules known to affect the gross physiology or the cellular physiology of the body, such as coagulation factors, hormones, antibodies and any molecules with known medical effects. One mechanism of action of such "blank" spheres would be their ability to directly capture or carry other biologically active molecules present in the blood. For example, if a sphere made in the present invention is capable of binding the fibrinogen molecule in the blood of the patient after infusion to the patient, then the combined product (the device with the active molecules in vivo) may have a medical effect on the body.

Of particular interest is that the spheres made with the present invention can bind fibrinogen long after their production date and under conditions very different from the conditions of synthesis. Thus, it is possible that the spheres can bind fibrinogen produced by the patient after infusion to the patient. Healthy patients have a concentration of (soluble) fibrinogen ranging from 1.77 to 3.75 mg per ml of plasma. Yet if the patient is thrombocytopenic, the bleeding time is still elevated, showing that normal concentrations of (soluble) fibrinogen cannot replace the function of adequate concentrations of platelets. However, spheres having endogenous fibrinogen bound in vivo can mimic activated platelets, having an effect unexpected of soluble or non-bound fibrinogen, but having an effect similar to that of transfused platelets.

Although serum albumin is described in this invention as the source material for the manufacture of the device, it is obvious to one skilled in the art that other protein molecules can be used.

Although the spheres described in this invention is capable of improving the bleeding time of a thrombocytopenic patient as if the patient had received a platelet transfusion, it is expected that the spheres can also bind other biologically active molecules in the body, such as any drugs present in vivo.

Although the product of the present invention is mainly spherical, it is expected that non-spherical particles can similarly be effective. The size of these devices, regardless of the overall shape, should not exceed 5 micron in any one dimension, including the diameter, to prevent obstruction of the blood capillaries. The biologic device should ideally be in the form of a suspension, being suspended in a medium compatible with intravenous administration to a patient. The biological device can be spherical, with a mean diameter of 0.3 to 0.5 micron, ideally less than 0.3 micron in diameter.

It is also important that the size and density of the particles should be small enough to remain in suspension by Brownian motion in the medium with which the particles or spheres are stored. This is to prevent sedimentation in the absence of an occasional shaking, which will lead to the formation of material at the bottom of the container, which is not suitable for intravenous administration to a patient.

The product made with the present invention can be given to any patient in need of platelet infusion for whatever reason when donor platelets are not available, whether from lack of donors, or insufficient infrastructure to harvest or maintain platelets, or a history of reaction to platelets or related blood products.

It is expected that the homeostatic condition of the patient is improved by administration of the device described in this invention.

The following are detail descriptions of experiments showing how the product is made and how it can be used.

EXPERIMENT 1

Manufacturing Protein Particles from Several Commercial Preparations of HSA

Purpose: To evaluate if 25% Human Serum Albumin (HSA) purchased from different suppliers are identical with respect to the formation of control protein particles (without the addition of other biological molecules in vitro) under similar conditions.

Rationale: Commercial manufacturers of HSA may have variations in their manufacturing steps including treatment with chemicals, temperature, sterilization conditions, filtration conditions, storage conditions, and added excipients, buffers, electrolytes and other material that can affect the condition of the protein solution to be used for manufacture of protein particles according to the present Invention. This experiment aims to discover and evaluate any such differences.

U.S. Pat. No. 5,069,936 discussed the importance of adding a detergent or surfactant to the protein solution before addition of the desolvation agent (Column 4, line 21 to 24.) One aim of the present experiment was to evaluate the effect of not adding any such detergent or surfactants to the protein solution, before or after addition of the desolvating agent.

Another aim of this Experiment was to evaluate the effect of adding various salt concentrations in the protein solution before addition of a desolvating agent.

U.S. Pat. No. 5,308,620 ("Protein Nanomatrixes and Method of Production) disclosed the effect of reducing the salt content of the 25% HSA in order to facilitate formation of spheres without aggregation (Experiment 13, Effect of osmolarity [hypotonicity] on synthesis of human serum albumin nanomatrixes, Column 19-22.) The overall conclusion was "by using HSA extensively dialyzed in water to remove practically all free sodium ions, useful nanomatrixes were obtained (Table 13) at HSA concentration as high as 110 mg/ml in conjunction with STS concentration of 7.7 mg/ml (Column 20, line 35-39.) In short, high sodium chloride content tends to result in "useless aggregates."

For the above reason, Experiment 1 was designed with the deliberate addition of sodium chloride molecules to the HSA solution which had not been previously dialyzed. The salt was added before the addition of ethanol (70% in water). The ethanol was used as a desolubilizer (or desolvation agent) to see which (if any) of the 5 different batches of HSA was most favorable for sphere or particle formation without aggregates.

Material and Method: Five batches of HSA (all 25%) were purchased respectively from Alpha Therapeutic Corp, Los Angeles ("A"); Baxter Healthcare Corp, Glendale ("B"); Central Lab, Blood Transfusion Service, Swiss Red Cross ("C"); Immuno-US, Inc. Rochester MI ("I"); ZLB Bioplasma, Switzerland ("Z"). Glutaraldehyde (GL) was purchased from Electron Microscopy Sciences (Fort Washington, Pa.)

The electrolyte contents of the various HSA were measured by a standard clinical laboratory chemistry panel and the results were displayed in Table 1.

An undialysed aliquot (32 microliter) of HSA (25%) was taken from a new bottle from each of the supplier of commercial HSA (25%). The aliquot was mixed at room temperature (19 to 23 deg C.) in a tube with 68 microliter of sodium chloride solution (Preparations called P, Q, R, S, T and W, representing solutions containing 9.0, 7.2, 5.4, 3.6, 1.8 and 0 mg of sodium chloride/ml in water, respectively) in the absence of any added detergent.

Therefore all 30 tubes (table 2) contained a uniform concentration of HSA at 80 mg/ml, but varying concentrations of sodium and chloride ions. Then 100 microliter of glutaraldehyde (GL 1.6 mg/ml in water) was added. This is similar to the "Prelink" method disclosed in the prior art, except for the short duration of GL interaction with the protein before addition of the ethanol, as noted below; and the absence of added surfactant or detergent in the protein solution. After thoroughly mixing the content in the tube, 333 microliter of ethanol (70% in water) was added within 15 seconds of the addition of GL to the protein solution and the mixture either turned turbid immediately, or remained transparent and clear.

To assess the size of particles formed, about 18 microliters of a suspension were placed on a microscope slide and observed under a cover slip in phase contrast at 1500 power magnification. The diameter of the most common population of spheres was compared with a standard micrometer placed inside the eye-piece. Typically by visual inspection, over 99% of the particles in any preparation were spheres. In preparations containing spheres of greater than 1 micron diameter, however, occasionally particles could be observed that were non-spherical which had the irregular shape like "potatoes" (which were less than 1% of the population by visual inspection.)

Results:

TABLE 1

Electrolyte contents of the various preparations of (undialysed, undiluted, original) HSA 25%

| Supplier | Sodium concentration millimolar | Chloride concentration, millimolar | $CO_2$ Concentration, millimolar |
|---|---|---|---|
| A | 138 | 61.4 | <3 |
| B | 133 | <48 | 18 |
| C | 133 | 68.2 | 3 |
| I | 138 | <48 | 5 |
| Z | 137 | 71.5 | 4 |

The result showed that while the sodium concentration was comparable for all 5 stock solutions, the chloride concentration varied from less than 48 millimolar to 71.5 millimolar, suggesting that the different stock solutions contain other anions for adjusting the pH of the stock solution to physiological pH. Similarly the bicarbonate ($CO_2$) concentration varied from less than 3 to 18 millimolar.

Table 2 showed the total chloride and sodium ion concentrations after dilution of the stock HSA solutions with different diluent sodium chloride solutions. These concentrations of chloride and sodium ions are the respective concentrations of ions in the protein solution before the addition of GL. Table 2 also showed the resultant products (spheres or aggregates) obtained from mixing the various solutions as described in the above Material and Method section.

In summary: Tube 1 to 6 contained albumin purchased from supplier A; tube 7-12 from supplier B; tube 13-18 from supplier C; tube 19-24 from supplier 1; tube 25-30 from supplier Z.

The total concentration of chloride ion in the protein solution before addition of GL was the sum of the contribution from the diluent and the contribution from the respective stock HSA (25%) after dilution. For example, in Tube 1: A volume of 68 microliter of Diluent P (9 mg NaCl/ml, or 154 millimolar) contributed 104.7 millimolar of chloride ions, as compared to 19.6 millimolar of chloride coming from 32 microliter of 25% albumin from supplier A (containing 61.4 millimolar chloride in the 25% stock solution.)

Regarding the concentration of sodium ions, since the concentration of sodium ion in the albumin stock solution varied only from 133 to 138 millimolar; the sodium ion concentrations in tube 1, 7, 13, 19, 25 are comparable (being 147 to 149 millimolar); that of tube 2, 8, 14, 20, 26 was 126-128 millimolar; that of tube 3, 9, 15, 21, 27 was 105-107 millimolar; that of tube 4, 10, 16, 22, 28 was 84-86 millimolar; that of tube 5, 11, 17, 23, 29 was 64-65 millimolar; that of tube 6, 12, 18, 24, 30 was 43-44 millimolar, respectively.

In terms of turbidity, all the tubes were turbid after the addition of the desolvation agent, except for tube 10, 11, 12 which remained transparent and clear.

Aggregates were observed in tubes diluted with high concentrations of sodium chloride solutions, except when using the 25% HSA stock solution purchased from Baxter.

Spheres were not produced from the 25% HSA stock solution purchased from Baxter when diluted with water, or with diluent S and T (tube 10, 11, 12.) The 25% HSA stock solution purchased from Baxter required dilution with a diluent containing a minimal concentration of sodium chloride (such as diluent P, Q, R) before spheres can be formed with this method.

Useful spheres (0.7 to 1 micron) without aggregates were produced with Baxter HSA25% under conditions of high sodium chloride concentrations (e.g. tube 7, 8, 9) where the products from HSA25% obtained from the other 4 suppliers uniformly formed useless aggregates (tube 1 to 3; tube 13-15; tube 19-21; tube 25 to 27.)

TABLE 2

Total concentration of chloride ions (mEq) and sodium ions (mEq) in each tube before the addition of the crosslinking agent, and certain properties of the sphere suspensions produced from the respective protein solutions.

| tube | diluent soln | [Cl] from diluent | [Cl] from stock albumin | Total [Cl] | Total [Na] | Most common diameter of spheres, micron | Presence of Aggregates |
|---|---|---|---|---|---|---|---|
| 1 | P | 104.7 | 19.6 | 124.3 | 149 | clumps | yes |
| 2 | Q | 83.8 | 19.6 | 103.4 | 128 | clumps | yes |
| 3 | R | 62.8 | 19.6 | 82.4 | 107 | clumps | yes |
| 4 | S | 41.9 | 19.6 | 61.5 | 86 | clumps | yes |
| 5 | T | 20.9 | 19.6 | 40.5 | 65 | 0.7 | no |
| 6 | W | 0 | 19.6 | 19.6 | 44 | 0.7 | no |
| 7 | P | 104.7 | <15.4 | <120.1 | 147 | 0.7 to 1 | no |
| 8 | Q | 83.8 | <15.4 | <99.2 | 126 | 0.7 to 1 | no |
| 9 | R | 62.8 | <15.4 | <78.2 | 105 | 0.5 to 1 | no |
| 10 | S | 41.9 | <15.4 | <57.3 | 84 | no sphere | no |
| 11 | T | 20.9 | <15.4 | <36.3 | 64 | no sphere | no |
| 12 | W | 0 | <15.4 | <15.4 | 43 | no sphere | no |
| 13 | P | 104.7 | 21.8 | 126.5 | 147 | clumps | yes |
| 14 | Q | 83.8 | 21.8 | 105.6 | 126 | clumps | yes |
| 15 | R | 62.8 | 21.8 | 84.6 | 105 | clumps | yes |
| 16 | S | 41.9 | 21.8 | 63.7 | 84 | clumps | yes |
| 17 | T | 20.9 | 21.8 | 42.7 | 64 | 1 | no |
| 18 | W | 0 | 21.8 | 21.8 | 43 | 0.3 | no |
| 19 | P | 104.7 | <15.4 | <120.1 | 149 | clumps | yes |
| 20 | Q | 83.8 | <15.4 | <99.2 | 128 | clumps | yes |
| 21 | R | 62.8 | <15.4 | <78.2 | 107 | clumps | yes |
| 22 | S | 41.9 | <15.4 | <57.3 | 86 | 0.7 to 1.2 | no |
| 23 | T | 20.9 | <15.4 | <36.3 | 65 | 0.5 to 0.7 | no |
| 24 | W | 0 | <15.4 | <15.4 | 44 | 0.5 | no |
| 25 | P | 104.7 | 22.9 | 127.6 | 149 | >1 | yes |
| 26 | Q | 83.8 | 22.9 | 106.7 | 128 | >1 | yes |
| 27 | R | 62.8 | 22.9 | 85.7 | 107 | >1 | yes |
| 28 | S | 41.9 | 22.9 | 64.8 | 86 | 0.7 | yes |
| 29 | T | 20.9 | 22.9 | 43.8 | 65 | 0.7 | yes |
| 30 | W | 0 | 22.9 | 22.9 | 44 | 0.5 | no |

Comments: The data showed a number of surprising results:

(1) U.S. Pat. No. 5,069,936 disclosed the importance of having a suitable concentration of surfactant or detergent in the protein solution before the addition of the desolvating agent (Column 4, line 20-35.) However, in the present experiment, none of the tubes have any added surfactant or detergent and yet spheres ranging from 0.3 to 0.7 micron in diameter could be produced without aggregates, apparently when the concentrations of sodium and chloride ions were appropriate. (For example, tube 5, 6, 7, 8, 9, 17, 18, 22, 23, 24, 30).

(2) Low concentrations of sodium ions appeared to be a favorable factor in the formation of spheres without aggregates in four out of five HSA stock solutions purchased from different suppliers. The exception was supplier Baxter, whose albumin stock solution could be used to form spheres without aggregation even in high concentrations of sodium ions (e.g. tube 7, 8, 9).

(3) The highest tolerable concentration of sodium ion in terms of the formation of spheres without aggregates varied from supplier to supplier. For example, in tube 4 (supplier "A") and in tube 16 (Supplier "C") clumps or large aggregates were observed if the sodium concentration was 84 mEq or higher. However, using HSA supplied by Immuno-US Inc. (e.g. tube 22) spheres were formed without aggregates even if the sodium concentration was 86 millimolar. In contrast, for protein solutions prepared from Baxter Healthcare Corp, if the sodium ion concentration was below 84 millimolar (tube 10, 11, 12) no spheres were formed. In fact, using the albumin stock solution from Baxter Healthcare Corp., spheres could still be synthesized without aggregates in sodium concentrations as high as 147 millimolar (tube 7) before the addition of the crosslinking agent and ethanol solution.

(4) The concentration of chloride ions did not appear to be decisive as to whether spheres could be formed without aggregates. Concentrations of chloride as low as below 15.4 millimolar (tube 24) and as high as below 120.1 millimolar (tube 7) were successful in producing spheres without aggregates when the stock solution was supplied by Supplier "I" and Supplier "B", respectively. In contrast, other tubes containing albumin solutions diluted from stocks provided by the other suppliers to intermediate ranges of chloride concentrations (e.g. tube 2, 3, 4, 14, 15, 16, 26, 27, 28, 29) resulted in clumps and aggregates.

(5) Surprisingly, the albumin stock solution purchased from supplier B, when the total chloride concentration was 57 millimolar or less, in conjunction with a sodium concentration of 84 millimolar or less (tube 10, 11, 12) produced no spheres; the solution remained clear after addition of the same volume of crosslinking agent and ethanol (70%) as added to other tubes. The manufacturer B disclosed that its product had been subjected to heat at 60 degree C. for 10 hours. The other manufacturers did not make similar disclosures. It is not clear if the unique pattern of sphere formation or the failure to form spheres (but no aggregates) is due to the manufacturing process of Baxter Healthcare Corp. as opposed to the methods used by the other suppliers.

(6) When all the sphere preparations without aggregates were examined carefully under the microscope, the spheres were observed to be monodisperse in size distribution. The exceptions were the preparations in tube 25, 26, 27 where the majority of spheres were about I micron (about 99%) but some spheres greater than 1 micron and less than 5 micron in diameter (less than 1%) were observed. These 3 suspensions were noticeably heterogenous in size distribution.

(7) In all preparations where the average diameter of spheres was about one micron, or less than one micron, the size distribution of spheres appeared to be homogeneous. There were no non-spherical particles observed in any of these preparations and none had spheres larger than 5 micron in diameter.

Discussion: The conditions for successful production of spheres of a narrow size distribution and without co-formation of aggregates in the suspension are very stringent. It is not possible to delineate all the potential reasons why this present method succeeded as described while the prior art failed to produce medically useful sphere suspensions.

As to the discovery that spheres could be formed in the present Invention without the addition of a detergent or additional surfactant to the protein solution, one reason or hypothesis could be the short duration (15 second) of GL interaction time with the protein molecules, after which the desolvation agent was added. The procedure disclosed in U.S. Pat. No. 5,069,936 (e.g. Example 4, Experiment 1 in Column 22, line 56 to Column 23, line 30) employed a much longer reaction time of GL with the protein molecules before addition of the desolvating agent (e.g. 5 minutes before the addition of a buffer, which interacted with the partially linked protein solution for another 5 minutes before the ethanol was added, i.e. a total of 10 minutes.)

U.S. Pat. No. 5,069,936 did not teach about the importance of a short "crosslinking agent interaction time" in the protein solution. It is conceivable that a long crosslinking time (e.g. 10 minutes) could have led to the formation ultimately of "gross, useless clumps" (Column 23, line 15), which could only be averted by the inclusion of a detergent in the protein solution prior to the addition of the desolvation agent.

Conclusion: Although all the evaluated 25% human albumin stock solutions (commercial albumin products approved by the FDA for clinical use) had comparable albumin concentration, sodium concentration and pH, they did not produce comparable suspensions of spheres when subjected to the novel "Pre-link" method described in this experiment.

Undialysed stock albumin solutions (25%) supplied by 4 commercial suppliers (except Baxter Healthcare Corp) diluted simply with water (with no added detergent or surfactant) could result in sphere suspensions without aggregates after the addition of a crosslinking agent and desolvation agent, using conditions disclosed in this experiment.

Of particular interest is the formation of useful sphere suspensions under these conditions where there was no surfactant or detergent added to the protein solution and when the "crosslinking interaction time" with the protein molecules was 15 seconds or less.

It is not obvious from an evaluation of the respective sodium and chloride concentration used in this experiment why certain conditions were favorable toward sphere formation without aggregate, while others led to no sphere formation, or in the opposite direction, the formation of aggregates.

The present method also produced spheres substantially smaller than 5 micron, without contamination by spheres (or particles) larger than 5 micron in diameter which in previous disclosed methods necessitated additional steps of removal of such large spheres or particulates.

Certain stock solutions of HSA (e.g. purchased from Baxter), contrary to previous teachings in disclosed patents, needed to be supplemented with a sodium chloride containing solution (which served an additional purpose of diluting the stock protein solution to the desirable initial concentration) before spheres can be formed.

The stock albumin solutions provided by different vendors may be uniquely different in how they were manufactured and they require different conditions of synthesis before spheres can be produced without aggregates. The resulting spheres may possess different in vitro or in vivo properties which may not be readily detectable by visual or other physical inspections. Animal studies, particularly in thrombocytopenic rabbits, may be the only way to evaluate any difference in the biological property of the various preparations.

EXPERIMENT 2

Manufacturing Protein Particles Using Three Novel Methods

Purpose: To develop new methods of synthesizing protein spheres essentially free of particles larger than 5 micron in any dimension and to assess the stability of the products Rationale: U.S. Pat. No. 5,069,936 disclosed two methods of protein sphere synthesis. The first method was called the "Pre-link" method (meaning the cross-linking agent was added before the appearance of turbidity, or the formation of the spheres.) It essentially involved (a) dissolving the protein molecules; (b) adding a cross-linking agent to link part of the protein molecules together before they are pushed together for further cross-linkage; (c) adding the surfactant to interact with the surface of the proteins; (d) adding the desolvation agent to push the particles together into the microspheres. (Column 4, line 53 to Column 5, line 7.) The crosslinking agent (glutaraldehyde,-GL) concentration used would result in stable spheres resistant to solubilization upon dilution of the desolvating agent (such as by water or additional steps of processing.)

U.S. Pat. No. 5,069,936 further disclosed a second method of synthesis; essentially involving (a) dissolving the protein molecules; (b) adding the surfactant; (c) adding the desolvation agent; (d) adding the cross-linking agent to internally cross-link the microspheres. This method was called "Post-link" (meaning the crosslinking agent was added after the formation of spheres.) The spheres, formed initially in the absence of a crosslinking agent would dissolve (resolubilize) when the suspension is subjected to dilution with water or during additional steps of processing. The cross linking agent was added to the sphere suspension to completely crosslink the structure of the individual spheres to stabilize them against resolubilization.

Both methods described in this prior art involved the addition of a surfactant or detergent to the protein solution before the addition of the desolvating or desolvation agent.

The suspension resulting from the disclosed "Post-link" method, however, contained many spheres larger than 5 micron, which was true whether the spheres were coated with fibrinogen or not. Indeed, U.S. Pat. No. 6,263,988 B1 disclosed that Control Sphere (CS) was manufactured with a method (Column 11, line 34-35) similar to TS 1, except that TS 1 had an additional step of coating the spheres with fibrinogen Column 10, line 50 to 61.) Furthermore, the addition of fibrinogen to the suspension to create TS 1 did not increase the sphere size or changed the size distribution (Column 24, line 16-17 stated "CS (not shown) looked like Lot K9401, i.e. many large spheres were present.") Consistent with that description, Table 11 of U.S. Pat. No. 6,264,988 B1, showed that K9401 contained at least 8.65 million spheres per ml (reconstituted suspension) of a size larger than 7 micron in diameter (column 24, line 52.) The same was expected of the CS produced by that method.

The rationale of the present experiment was to compare three products made with the present Invention where no detergent or surfactant was added to the protein solution. The first product was produced by a novel method also called the "Pre-link" method (except for having no added detergent in the protein solution in the present Invention and a short cross-linking agent interaction time" of typically less than one minute). The second product was produced by a method also called the "Post-link" method (also without added detergent in the protein solution and using a short "cross-linking agent interaction time.")

The third product was produced by a novel "Mid-link" method, which was not previously described in any prior art. In this "Mid-link" method, the crosslinking agent was first pre-mixed with the desolvating agent and then the mixture was added to the protein solution (in the absence of added surfactants or detergents.) Therefore, the crosslinking agent was added at the same time as the desolvating agent. The initiation of the crosslinking action by the crosslinking agent on the protein molecules would start at the same time as that of the desolvating agent in forming the spheres from the soluble protein molecules. The effect of adding a crosslinking agent at precisely the moment spheres were formed from soluble protein molecules could not be predicted from either the "Pre-link" or "Post-link" method. Only detail animal studies could reveal the biocompatibility of the "Mid-link" spheres and the effect of using them for delivery of other biological or chemical molecules, or used alone.

The present experiment aims at evaluating both the effectiveness of this "Mid-link" method in producing medically useful spheres with no aggregates and how soon the product could be stabilized against resolubilization when the suspension was diluted.

Material and Methods:

HSA 25% was purchased from Alpha Therapeutics Corp, Glendale and diluted with water to 6% without the addition of detergents or other surfactants. Even though the term "Pre-link" and "Post-link" were similar to those in previously disclosed art, the methods used here are novel in that no surfactant or detergent were added to the protein solution at any time of the process of sphere formation and a short "cross-linking agent interaction time" (of less than 15 seconds) was used.

(a) The novel "Prelink" method: 200 microliter of HSA 6% (diluted with water from the 25% commercial HSA) was placed in a polypropylene microcentrifuge tube, to which 200 microliter of glutaraldehyde, GL (1.6 mg/ml in water) was added and shaken. Within 30 seconds, 640 microliter of ethanol (70% in water) was added and the mixture turned turbid. Final concentration of GL in the suspension was 0.31 mg/ml.

(b) The novel "Postlink" method: 400 microliter of HSA 3% (diluted with water from the 25% commercial HSA) was placed in a polypropylene microcentrifuge tube, then 640 microliter of ethanol (70% in water) was added and the mixture turned turbid. After 5 minutes, the suspension was added 52 microliter of GL (6.5 mg/ml.) Final concentration of GL in the suspension was 0.31 mg/ml.

(c) The novel "Midlink" method: 400 microliter of HSA 3% (diluted with water from the 25% commercial HSA) was placed in a polypropylene microcentrifuge tube, then 640 microliter of a solution (70% of ethanol in water, also containing 0.5 mg GL/ml) was added. The mixture turned turbid immediately. Final concentration of GL in the suspension was 0.31 mg/ml.

To assess the effectiveness of GL to completely crosslink and stabilize the particles against resolubiliztion at various time points, in accordance to the three novel methods described above, the following was done. For each of the above methods, an aliquot of the product (40 microliter) was removed at various times after the addition of the desolvation agent and diluted with 160 microliter of water. After one hour, the suspensions in all the tubes were centrifuged in a microcentrifuge (five minutes, top speed) to remove any stable spheres which had not redissolved. The protein concentration of the supernatant was measured by the BCA method (Pierce Corp.)

The concentration of spheres produced (mg/ml) was obtained from the difference between the final concentration of the albumin after addition of all the reagents (in all cases, 12 mg of albumin divided by the final volume of the suspension, which was 1040 microliter) and that of the concentration of soluble protein measured from the supernatant (after correction of the five-fold dilution with water for the purpose of redissolving any spheres which had not been stably crosslinked at that time point.) The "yield" of stable spheres is the concentration of the spheres produced, divided by the final concentration of the albumin molecules after addition of all the reagents to make the sphere suspension.

Results: The kinetics of stabilization with GL using the novel "Pre-link" method was similar to that using the novel "Post-link" method. Both achieved maximal stabilization within 4 minutes after the addition of ethanol. The maximum yield (plateau) appeared to be about 36% of all the available albumin molecules (sum of all the albumin molecules still in solution plus those in the sphere form) in the suspension. In contrast, spheres produced by the novel "Mid-link" method required more than 8 minutes to achieve maximal stabilization against resolubilization. The highest yield was about 37%.

Table 3 listed the percent yield of spheres at various times of dilution, of the spheres made with the "Pre-link" and the "Mid-link" method. (Data from Post-link method was similar to that of the Pre-link method and not included here.)

TABLE 3

Yield of Stabilized Spheres by the Pre-link and the Mid-link Method At Various Times After Appearance of Turbidity

| Time of dilution (min) | % Yield, Pre-link Method | % Yield, Mid-link Method |
| --- | --- | --- |
| 0 | 0 | 0 |
| 4 | 33 | 6 |
| 8 | 37 | 29 |
| 12 | 34 | 33 |
| 16 | 34 | 36 |
| 20 | 35 | 37 |
| 24 | 35 | 35 |
| 28 | 36 | 34 |

To evaluate the size distribution of spheres produced by the 3 methods, aliquots of stable spheres (after 28 minutes of stabilization) were observed under a phase microscopy. The spheres prepared by the "Pre-link" method were most commonly 0.3 micron in diameter, very uniform in size, with no aggregates, containing no spheres larger than 5 micron and no non-spherical particles.

The spheres produced by the "Post-link" method were about 0.1 micron in diameter, individual spheres were very difficult to see because of the Brownian movement, but obviously no aggregates, no spheres larger than 5 micron and containing no non-spherical particles.

Of interest are the spheres prepared by the "Mid-link" method under these conditions: the majority (over 99.9%) were 0.5 micron in diameter, but there was a distinct minority population (estimated to be about 10,000 per ml with a hemocytometer) that were larger than 5 micron in diameter, some reaching up to 15 micron in diameter. This concentration of "spheres larger than 5 micron" was about three orders of magnitude less than that observed in K9401 (U.S. Pat. No. 6,264,988 B1, table 11) and its comparable CS; and therefore may be acceptable for intravenous applications using low doses. There were no aggregates observed in the product made with the "Mid-link" method, nor particles with non-spherical shapes.

Conclusion: The products from the three methods are different even though the concentration of albumin at the time of the addition of ethanol was the same and the final concentration of the crosslinking agent was identical. Other conditions of synthesis using the novel "Mid-link" method needed to be explored (to be described below) to avoid the presence of spheres larger than 5 micron during synthesis in order to produce a suspension suitable for intravenous medical applications with a high degree of safety.

EXPERIMENT 3

Refinement of the "Mid-link" Method to Avoid Production of Spheres Larger than 5 Micron During Synthesis Purpose: To find improved conditions of synthesis where the product from the novel "Mid-link" method is not hetergenous in size distribution. In particular, the suspensions produced would not have any spheres or particles larger than 5 micron in diameter.

Rationale: Data disclosed in U.S. Pat. No. 5,069,936 indicated that a higher initial concentration of albumin (e.g. from 40, 60 to 80 mg/ml; table in Experiment 5, column 25) would result in larger spheres (at every concentration of added detergent.) Also, U.S. Pat. No. 6,264,988 B1 disclosed the presence of 6.48 billion very large spheres/ml (with diameter greater than 10 micron; Table 12, column 26) when the initial concentration of albumin used was 15% (TS 1, column 10, line 38; purchased from Alpha Therapeutics, Calif.) Therefore it was expected that more "large spheres" (defined as spheres larger than 5 micron in diameter) would result if an initial concentration higher than 3% albumin was to be used in the synthesis of spheres using the novel "Mid-link" method.

Material and Method: The described "Mid-link" method as described in Experiment 2 was repeated except with higher concentrations of HSA (ranging from 5% to 6% of HSA purchased from supplier A and diluted only with water, without surfactant or detergent added.)

Results: The spheres formed within this range of albumin concentrations were consistently 1 to 2 microns, with no observable spheres larger than 5 micron, no aggregates, and no particles of irregular or non-spherical shape.

Conclusion: Although data from a previously disclosed patent (U.S. Pat. No. 5,069,936) using a Pre-link method and a Post-link method (U.S. Pat. No. 6,264,988 B1) (both with added surfactant) would suggest that higher initial concentrations of albumin would more likely produce spheres larger than 5 micron in diameter, the opposite effect (compared to the product synthesized with 3% albumin solution) was obtained by using a higher concentration of albumin (5% and 6% diluted in water) when produced by the novel Mid-link method.

Although most of the spheres were 1 to 2 micron in size in this experiment (as compared to an average of 0.5 micron in experiment 2) there were no spheres or particles larger than 5 micron present. Therefore, the appearance of a minority population of large spheres (greater than 5 micron in diameter) is not correlated in the "Mid-link" method with the average size of the majority population. An overall increase in size of the majority population was not correlated with any appearance of the physiologically unsafe subpopulation of large spheres.

EXPERIMENT 4

Binding of Fibrinogen Molecules to Spheres Produced by Different Methods

Purpose: To evaluate if the spheres prepared by the novel Post-link and the novel Mid-link method can both bind fibrinogen by mixing with a fibrinogen solution, without the need to add additional crosslinking agents and without resulting in the formation of aggregates in the fibrinogen-containing suspension Rationale: Experiment 2 showed that spheres prepared by the Pre-link and Post-linked method required at least 4 minutes before the crosslinking agent could stabilize the spheres with maximal effect. Mid-link method needed more than 8 minutes. Other preliminary experiments had suggested that glutaraldehyde molecules attach to protein molecules very quickly and the reaction would have completed within minutes (data not shown here). To further minimize any effect from glutaraldehyde in the suspension, fibrinogen molecules were added in this experiment to the turbid suspension at least 10 minutes after appearance of turbidity in the preparation when little or no "still reactive" glutaraldehyde molecules are present.

Commercial supplies of fibrinogen are typically lyophilized power formulations containing a high concentration of salt (e.g. 15% sodium citrate and 25% sodium chloride, see Product F3879 from Sigma-Aldrich Co.) Addition of such a high concentration of salt may lead to aggregation of spheres even though the preparation may be stable in the absence of such added salt derived from the fibrinogen solution. This experiment aims to evaluate the proper dilution of commercial supplies of fibrinogen which would still allow enough fibrinogen to be bound to spheres to have medicinal value without causing aggregation of already formed spheres in the suspension.

Material and Methods: Human Fibrinogen powder was purchased from Sigma-Aldrich Co. and dissolved in normal saline (0.9% sodium chloride) to 1 mg clottable protein/ml before mixing with sphere preparations at a ratio of 0.5 ml to 1.0 ml of fibrinogen solution per 1.0 ml of sphere suspension. Fibrinogen supplied by other suppliers are expected to be similarly effective.

Post-link albumin spheres were prepared as close to the method described for TS1 in U.S. Pat. No. 6,264,988 B1 as possible except (1) no detergent was added to the protein solution, (2) the solutions were mixed in rigid plastic tubes instead of inside a silicone tubing system, (3) a different ratio of the volume of fibrinogen solution added per volume of the sphere suspension was used here as described above.

Mid-link spheres were prepared as in Experiment 3, again without the addition of a detergent to the protein solution, followed by the addition of the fibrinogen solution to the turbid sphere suspension 10 minutes after the appearance of turbidity.

Both Post-link and Mid-link sphere preparations were centrifuged to remove the ethanol and any residual crosslinking agent or fibrinogen in the supernatant. The pellet was resuspended in normal saline.

To evaluate if fibrinogen coated spheres could form thrombin-induced aggregates in vitro, the method previously described was used. Aggregation of particles under "sub-minimal" concentrations of soluble fibrinogen was previously described in U.S. Pat. No. 6,391,343 B1 "Fibrinogen-Coated Particles for Therapeutic Use" Column 19, line 47-60. Essentially, fibrinogen solutions at low concentrations that normally do not form a visible clot ("sub-minimal" concentration) on addition of thrombin (3 units per ml) were mixed with Control Spheres (CS) or spheres previously coated with fibrinogen. Then thrombin was added. CS do not have fibrinogen on their surface and had been shown in the prior art not to form aggregates on the addition of thrombin to the mixture under these conditions. Spheres previously coated with fibrinogen, however, will form aggregates when suspended in a "sub-minimal" concentration of fibrinogen, after the addition of a thrombin solution.

Result:
Addition of a fibrinogen solution (diluted with normal saline) to the sphere suspensions under the conditions of this experiment did not result in aggregate formation from the salt introduced with the fibrinogen solution.

Both fibrinogen-coated-Post-link spheres and fibrinogen-coated-Mid-link spheres form aggregates in the presence of a sub-minimal concentration of fibrinogen, after the addition of a thrombin solution, as described. The data showed that Mid-link spheres could bind fibrinogen to a similar extent as the Post-linked spheres; and both sphere preparations may be effective in treatment of thrombocytopenic animals.

Control Post-link spheres and control Mid-link spheres, both without added fibrinogen before mixing with the sub-minimal concentration of fibrinogen solution did not form thrombin-induced aggregates under these conditions.

Comments:
Data from preliminary experiments (not shown here) had indicated that binding of GL to protein molecules could complete in less than 5 minutes. Since the fibrinogen molecules were mixed with the spheres in this experiment after 10 minutes of the appearance of turbidity, the binding of fibrinogen molecules to spheres probably did not require or depend on the presence of still reactive, residual amount of crosslinking agents (i.e. any leftover from what was needed to stabilize spheres against resolubilization.) The attachment of fibrinogen molecules to these spheres could be non-covalent.

Fibrinogen-coated-Post-link spheres prepared by the prior art in the presence of a detergent in the protein solution (such as TS 1) could form thrombin-induced sphere aggregates in vitro in sub-minimal concentrations of fibrinogen. Those spheres could also form co-aggregates with human platelets after the addition of aggregation agents such as ADP or collagen in vitro (FIG. 13B, in U.S. Pat. No. 6,264,988 B1.) Therefore, the ability of fibrinogen-coated-spheres made by both the novel Post-link and the novel Mid-link method to form thrombin-induced sphere-sphere aggregates (from single spheres produced by the Mid-link methods) in the presence of sub-minimal concentrations of fibrinogen suggested that fibrinogen-coated-spheres made with these two novel methods would be capable of forming similar co-aggregates with human platelets in vitro and also in vivo.

The failure of control spheres, made by either the novel Post-link method or the novel Mid-link method to form thrombin-induced sphere aggregates suggested under these conditions of low fibrinogen ("sub-minimal") concentrations, both kinds of spheres either did not bind or did not bind enough fibrinogen molecules to be effective in forming sphere-to-spheres aggregates after the addition of thrombin.

Conclusion: The novel "Mid-link" method could produce spheres approaching the size of natural platelets (which are about 2 micron) without the co-production of large spheres (larger than 5 micron.) The binding of fibrinogen to spheres at a time point when the crosslinking agent would have been exhausted (from having completely bound to the albumin molecules, either in the sphere form or in the residual soluble form) suggested that the binding of fibrinogen to spheres needed not be covalent for the combination to be effective in providing medicinal value.

EXPERIMENT 5

Manufacturing Protein Spheres Using a Novel Bi-link Method

Purpose: To develop a new method of producing high concentrations of spheres essentially free of spheres larger than 5 micron in diameter, by the use of high concentrations of protein solution and two doses of crosslinking agents.

Rationale: Experiment 2 showed that both "Prelink" and "Postlink" methods could produce sphere suspensions with no spheres larger than 5 micron. However, to achieve that goal, the initial protein concentration had to be relatively low (e.g. 3% at the time when desolvation agent was added.) As a result the concentration of spheres in the final suspension was also relatively low.

Since there are occasions where a high concentration of spheres is desirable, one approach would be to start with a low initial protein concentration, form the relatively uniform spheres and then concentrate the spheres in the product by filtration to remove excess fluid. Filters, however, are easy to clog and had been shown to alter the property of the product to be filtered (U.S. Pat. No. 6,264,988 Table 13.) Therefore the present experiment attempts to investigate a new method using a relatively high concentration of protein solution, but employing a crosslink agent in two steps, initially with a "sub-effective" (also called "sub-stabilizing") concentration and then with a "stabilizing" concentration. The "sub-effective" concentration was defined as the concentration of crosslinking agent at which or below which spheres would re-dissolve when the desolvating agent was diluted. In this sense, the "sub-effective" dose was actually a "sub-stabilizing" dose. The "stabilizing" concentration was the concentration of crosslinking agent present at which or above which spheres would be stabilized against resolubilization.

The "Bi-link" method is novel because prior to these experiments, the addition of a "sub-stabilizing" dose of crosslinking agent was meaningless because there would not be any stable sphere products formed. Addition of another dose of crosslinking agent was not previously considered because the time interval between the doses may be important to the properties of the spheres and it was not clear whether the suspension would still contain single, monodispersed spheres after a second and higher concentration of crosslinking agent (the "stabilizing" concentration) was added to the suspension.

In this experiment it was found that a sub-stabilizing concentration in fact had an effect independent of its effect on the resolubilization of the spheres. A sub-stabilizing dose had an unexpected effect on increasing the homogeneity of the sphere size distribution.

Utilization of this step (adding a sub-stabilizing concentration before the formation of spheres, to be followed by a "'stabilizing" concentration of crosslinking agent after the appearance of the spheres) eliminated the formation of the minority population of spheres which exceeded 5 micron in diameter. Without the use of this step, under otherwise identical manufacturing steps, spheres larger than 5 micron would result in the mixture, even when the great majority of the spheres were much less than 5 micron in diameter.

Theoretically, there are two time-points where the substabilizing dose of crosslinking agent could be added. The sub-stabilizing dose of crosslinking agent may (A) be added to the soluble protein solution before the addition of the desolvation agent, or (B) it could be added after the appearance of turbidity (after the addition of the desolvation agent) but before the addition of the stabilizing concentration of the crosslinking agent. In either case, the turbidity would disappear upon dilution of the suspension (by a solvent not containing any desolvation agent) unless as stated, a subsequent "stabilizing" dose of crosslinking agent was added (before dilution or removal of the desolvation agent.)

However, it was found that if the sub-stabilizing dose was added to the protein solution after the desolvation agent was added as discussed in option (B) in the previous paragraph (but before the stabilizing dose of crosslinking agent was added) spheres larger than 5 microns were already formed. Therefore such an approach would only produce heterogenous populations containing large spheres, since the spheres would not redissolve once the stabilizing dose of crosslinking agent was added.

Therefore, in these experiments the sub-stabilizing dose of crosslinking agent was always added to the soluble protein solution before the addition of the desolvation agent, followed later by a second dose of stabilizing concentrations of crosslinking agent.

The second dose of crosslinking agent was called in this Invention as the "stabilizing" concentration of crosslinking agent. The agent could be the same chemical entity as the "sub-stabilizing" agent or a different chemical or agent. This dose was needed to create stable spheres and it was not related to the use of a "second dose" of crosslinking agent as described in U.S. Pat. No. 5,069,936, Example 14 which was used to covalently bind other biological molecules to spheres that were already stabilized.

The in vivo effects of the various methods of crosslinking the protein molecules within spheres and how the individual protein molecules are folded into the spheres are at present unknown and can be evaluated only with animal studies, particularly thrombocytopenic animals. Therefore, this "Bi-Link" method should be regarded as non-obvious and cannot be regarded as merely the combination of the "pre-link" and the "post-link" method.

Material and Method:

Part A: Assessment of the concentration of crosslinking agent which was sub-stabilizing under the conditions used. HSA 25% purchased from supplier Z was diluted with water to 12% without addition of any detergents or other surfactants and without further addition of any salt solution. Solutions of glutaraldehyde (GL) were prepared by dilution of stock GL (10%, purchased from Electron Microscopy Sciences, Fort Washington. Pa) with water to the following concentrations: 1.6, 0.8, 0.4, 0.2, 0.1, 0.05, 0 mg/ml, respectively. In a series of tubes, 200 microliter of HSA (12%) were mixed with 200 microliter of GL (of various known concentration.) Ethanol (70% in water, 720 microliter) was added within 15 seconds. A sample was taken to observe under phase contrast microscopy if there were particles formed larger than 5 micron diameter. After another 10 minutes, 200 microliter of the turbid suspension was added to 400 microliter of water to see if the turbid suspension became clear. No stabilizing dose of GL was added in this portion of the experiment.

The "yield" of spheres in each tube which were resistant to resolubilization was measured as follows: An aliquot containing 200 microliter of each of the product after dilution with water (whether clear or still turbid) was centrifuged to remove the spheres. Then the concentration of soluble protein left in the supernatant was assayed. The concentration of protein in the supernatant from the control tube (with no crosslinking agent added and where all the spheres formed after the addition of ethanol were completely redissolved after water was added) was used as the "total protein concentration." All protein concentrations were measured by the BCA method (Pierce Corp.) The "yield" of spheres in a tube was the "total protein concentration minus the supernatant protein concentration in the tube" divided by the "total protein concentration."

Part B: Production of spheres stable against resolubilization using the Bi-link method involved a sub-stabilizing dose of GL (0.1 mg/ml) and a stabilization dose of GL (12.5 mg/ml.) Essentially the same manufacturing steps were used as in Part A, except that following the addition of ethanol to form (still unstable) spheres, a stabilizing concentration of GL was added. To evaluate the effect of adding the stabilizing concentration of GL at various times, the stabilizing dose was added at 2, 4, 6, 10 or 15 minutes after the addition of ethanol. The stabilizing concentration of GL was added at a ratio of 45 microliters per 1120 microliter of the turbid suspension. Thereafter the suspensions were challenged by dilution with water 10 minutes after the addition of the stabilizing dose of GL and the yield of sphere suspensions were performed as described.

Spheres produced by this Bi-link method were frozen after a suitable excipient was added, or lyophilized. Appearance and property of spheres after thawing of the frozen sample, or reconstitution of the lyophilized powder with water were evaluated.

Result:

Part A: On dilution with water, all the turbid suspensions turned clear except for those two tubes where the initial concentration (before mixing 1:1 with the protein solution) of GL was 1.6 and 0.8 mg/ml, respectively. The yield of spheres was over 25% when the initial dose of GL was 1.6 and 0.8 mg/ml. The yield dropped to 5% when the GL concentration was 0.4 mg/ml, and to below 1% with any initial concentration of GL below 0.4 mg/ml. Therefore the "sub-stabilizing" concentrations of crosslinking agent under the described concentrations of ingredients and steps of mixing were determined to be 0.4 mg/ml of GL, or lower.

It was also found that the addition of a sub-stabilizing concentration of GL (from 0.4 to 0.05 mg/ml in water) had an effect on preventing the formation of a minority population of large spheres after the addition of the desolvation agent (with or without the addition of the stabilizing dose of GL.) The suspensions when observed undiluted under the microscope were homogenous in size distribution and did not have large spheres.

Moreover, it was observed that the typical size of the spheres formed after addition of a dose of GL (followed by the ethanol) was about the same regardless of the concentration of the first dose of GL used (ranging initially from 1.6 mg/ml to 0.05 mg/ml.) All the suspensions (observed undiluted) had spheres about 0.8 to 1.2 micron in diameter as evaluated by phase contrast microscopy. There were no particles or spheres larger than 5 micron in all the tubes, except for the control tube where no GL was added. In the control tube, the majority of spheres were larger than 1 micron and spheres larger than 5 micron were observed at about a concentration of 10,000 per ml.

Part B: The yield of the suspensions after a stabilizing dose of GL was added was over 25% in all tubes, including the control tube. Addition of the stabilizing dose of GL at 2 minutes after the addition of ethanol resulted in suspensions with comparable concentrations of spheres as those added at 15 minutes after the addition of ethanol. The data suggested that it took not more than 2 minutes for the stabilizing concentration of GL to effectively stabilize the spheres in the suspension.

Microscopy evaluating the size distribution of spheres after the addition of the stabilizing concentration of GL (12.5 mg/ml) showed that this follow-up step did not alter the size of the spheres, or produce aggregates. All the suspensions in all the tubes with the first dose of GL (ranging from 1.6 mg/ml to 0.05 mg/ml) did not have spheres larger than 5 micron, nor aggregates after the addition of the desolvation agent. After addition of the stabilizing concentration of GL, there was no change in the size distribution of all the suspensions.

Addition of the stabilizing dose of GL to spheres in the control tube (no GL in the first dose) after addition of the desolvation agent rendered the spheres insoluble upon dilution with water but kept the same size distribution in this preparation (with spheres larger than 5 micron observed.)

Addition of a suitable excipient which included a mixture comprising of maltose (from 18 to 28 mg/ml), lactose (from 18 to 28 mg/ml) and glycine (from 0.5 to 1.5 mg/ml) in the sphere suspension before freezing at −18 C or lyophilization preserved the size distribution of the spheres in the suspensions. It resulted in no change in the appearance or property of the suspensions after thawing of the frozen samples or reconstitution with water of the lyophilized product.

Comments and Conclusion: The presence of a small population of "large spheres" (larger than 5 micron in diameter) as described in U.S. Pat. No. 6,264,988 B1 (e.g. Lot K9401) may be tolerated by the subject when a low dose of the spheres was administered. With high doses it would be advantages to administer suspensions with minimal amounts of, or no detectable concentrations of spheres or particles larger than 5 micron.

The present approach revealed a surprising finding that while a low dose (sub-stabilizing) of crosslinking agent could not prevent the resolubilization of the spheres upon dilution or upon removal of the desolvation agent, its presence and action had the unexpected effect of making sphere sizes more uniform. Such elimination of the spheres larger than 5 micron had great medical benefit. This suspension of sub-stabilized spheres could be permanently stabilized by a follow-up dose of crosslinking agent (at the stabilizing concentration) without disturbing or changing the relatively uniform size distribution of sphere, with the additional benefit of the spheres not dissolving upon further processing steps, including freezing or lyophilization.

EXPERIMENT 6

Albumin Spheres Coated with Multiple Human Clotting Factors, in vitro

Purpose: To evaluate if spheres exposed to human plasma can simultaneously bind multiple clotting factors from the plasma.

Rationale: In previous experiments, fibrinogen (also known as Factor I) was purchased from Sigma, e.g. F3879 which contained about 60% protein by weight, of which over 80% of the protein is clottable; the remainder being sodium citrate and sodium chloride.

The powder was typically dissolved in normal saline and added to the suspension of spheres to achieve coating of fibrinogen on the surface or imbedding within the matrix of the spheres.

The present experiment aims at evaluating whether more than one clotting factor could bind to spheres spontaneously when spheres were exposed in vitro to human plasma containing the full complement of coagulation factors.

Material and Methods:

The novel "Pre-link" method without the addition of surfactants was used. HSA 25% purchased from supplier A was diluted with water to 10% without addition of detergents or any other surfactants. To 4 ml of this protein solution in-a tube, 4 ml of GL (1.6 mg/ml dissolved in water) was added and mixed well by shaking. After 30 seconds, 12 ml of ethanol (70% in water) was added and the mixture turned turbid. The room temperature was about 21 degree C. Temperatures of 19 degrees C. to 23 degrees C. are acceptable.

Plasma was obtained from a healthy volunteer after removal of all cellular elements from the heparin-anticoagulated whole blood. The plasma contained 2.17 mg of fibrinogen/ml; and normal ranges of vonWillibrand Factor (vWF) and Factor IX.

Fibrinogen concentration was measured by a competitive immuno-assay. Fibrinogen standards purchased from Sigma-aldrich were diluted to a range of 0 to 5 microgram/ml with normal saline containing 10% Blocking Agent (purchased from Pierce; the solution was called NSB in these experiments.)

Spheres to be assayed for their bound-fibrinogen content were likewise diluted to a range of expected fibrinogen concentrations (in the sphere-bound form) suitable for the assay. Goat anti-human-fibrinogen antibody (called GAF here) and rabbit anti-Goat-IgG linked to peroxidase enzyme (called RAG here) were purchased from Sigma-aldrich and diluted to 1:3000 and 1:2000 solutions, respectively (with NSB.) An aliquot of antigen (either standard solution, or spheres; typically 25 microliter) was mixed with 100 microliter of GAF (containing excess antibody with respect to the added antigen.) After incubation, 100 microliter of the mixture was added per well in a 96-well plate. The wells had been pre-coated with a saturating concentration of fibrinogen. The excess GAF (leftover after some had bound to the fibrinogen on the spheres) would then bind to the fibrinogen pre-bonded on the plastic well. After adequate rinsing, 100 microliter of RAG was added. After further adequate rinsing, the substrate for peroxidase was added to generate a yellow color reaction. The sample with the highest fibrinogen concentration would have removed the largest amount of GAF (from the excess concentration) and thus have the least leftover to bind to the plastic well. Therefore, the higher the fibrinogen content (whether in the soluble form or attached to a sphere surface or interior) in the sample, the lighter the color in the well. Comparison of the color optical density (in a spectrophotometer) with the color optical density of standard solutions generated the concentration of fibrinogen in the sample of interest.

Since there are no commercial supplies of purified human vWF or human Factor IX available to bind to plastic wells (as was possible with fibrinogen) the assay of these clotting factors (attached to spheres) required an indirect method of first "converting" the specific human antigen to a rabbit IgG marker. Rabbit anti-vWF (F 3520) and rabbit anti-Factor IX (F0652) and rabbit non-specific IgG (I5006) were purchased from Sigma-aldrich. Appropriate concentrations of these respective antibody solutions were prepared by dilution with NSB. Then 100 microliter of the respective antibody was mixed with 100 microliter of spheres. Subsequently the excess (still soluble) antibody was removed by centrifugation of the sphere suspension. The spheres were resuspended in normal saline, and they were by now coated with the specific rabbit antibody, if the spheres had the vWF or Factor IX to start with. This treatment converted the amount of specific antigen on the spheres (whether vWF or Factor IX) to an equivalent amount of a generalized antigen of rabbit IgG bound to the spheres.

The resuspended spheres were then subjected to a competitive immunoassay to measure the amount of rabbit IgG bound to the spheres (via the human vWF or Factor IX on the spheres). The antibody used was a goat anti-rabbit antibody (GAR, in excess amounts) which was already linked with a peroxidase enzyme. Left over GAR (not bound up by rabbit IgG on the sphere) was then added to plastic wells pre-bonded with non-specific rabbit IgG. For standard solutions, non-specific rabbit IgG was diluted to a range from 5 to 200 microgram/ml to react with GAR. The amount of GAR bound on the plastic well surface was measured by the addition of a peroxidase substrate.

Results:

Aliquots of albumin sphere suspensions (200 microliter) prepared with the "Pre-link" method as described were mixed (within 20 minutes after addition of ethanol) with the donor's plasma (diluted with water to achieve a fibrinogen concentration of 1.5 mg/ml in plasma, 160 microliter.) For comparison, another aliquot of the same suspension (200 microliter) was mixed with 160 microliter of purified fibrinogen (also 1.5 mg/ml.) After mixing, the suspension contained about 6 mg of spheres/ml.

The fibrinogen content on spheres coated with plasma and with the purified fibrinogen solution was found to be 20.4 and 18.1 ug fibrinogen/mg spheres, respectively.

The amount of specific rabbit antibody bound for the VWF and the Factor IX was found to be 5.2 ug per mg sphere and 0.47 ug per mg sphere, respectively, under the experimental conditions used.

Comments and Conclusions:

The data showed that endogenous fibrinogen molecules from plasma could bind spontaneously to spheres with the same efficiency as purified fibrinogen preparations obtained from commercial sources. When plasma was used, additional coagulation factors could bind simultaneously. In this experiment only fibrinogen, vWF and Factor IX were studied (as examples of coagulation factors) because antibodies to these factors were commercially available. It is expected that other coagulation factors or even non-coagulation factors, protein or non-protein molecules could bind to the spheres when spheres were mixed with whole blood.

The fact that 0.47 ug equivalent of rabbit IgG (anti-Factor IX) was bound per mg sphere compared to 5.2 ug equivalent of rabbit IgG (anti-vWF) does not mean that fewer IX Factor molecules were bound per mg sphere as compared to vWF molecules. The specificity of binding of the specific antibody (ug of antibody binding to one mg of antigen) to the respective antigen was not known and can be very different for these two antibodies and antigens.

The "Pre-link" method in this experiment was novel because no detergent was added to the protein solution before addition of the desolvation agent. Also a short "crosslinking agent reaction time" of 30 seconds with the protein molecules was used. Compared to the GL interaction time used in disclosed previous patents, 30 seconds was a short time. The suspension contained no spheres of larger than 5 microns and no aggregates.

Although only the novel method of "Pre-linked" spheres were tested in this experiment, it is expected that spheres produced by the novel method of "Post-link" and "Mid-link" and "Bi-link" and "BiMid-link" (all without added surfactant) are all capable of binding multiple coagulation factors and other biological molecules or drugs upon contact with plasma in vitro and in vivo.

It is expected that spheres containing a combination of multiple coagulation factors may have at least comparable or even superior medical efficacies as compared to spheres containing only bound fibrinogen.

EXPERIMENT 7

Synthesis of Albumin Spheres Using the Bi-link Method Followed with Coating with Various Concentrations of Fibrinogen Purpose: To manufacture a number of sphere preparations containing increasing concentrations of fibrinogen using the Bi-link Method and a supplier other than Alpha Therapeutics, California, for the purpose of evaluating whether a minimal amount of bound fibrinogen on the spheres is needed for improvement of bleeding time in thrombocytopenic rabbits.

Rationale: Yen disclosed a detail description of manufacturing spheres (U.S. Pat. No. 6,264,988 B1 "Fibrinogen-Coated Microspheres) coated with fibrinogen which resulted in improvement of bleeding time in thrombocytopenic rabbits (FIGS. 4, 5, 6.) HSA used to produced spheres in that disclosure was purchased from Alpha Therapeutics, Calif (Column 10, line 1.) It was not clear if the beneficial properties were the specific results of using HSA from this supplier as a source material. Since Baxter Healthcare Corp's product ("Buminate") appeared to differ the most (in terms of chloride and bicarbonate concentrations) from the HSA supplied by Alpha Therapeutics (see experiment 1), Buminate was used to produce particles in the present experiment, which would be further evaluated (described in Experiment 8) in thrombocytopenic rabbits.

In addition, previous fibrinogen-coated albumin spheres had all been prepared in the presence of a surfactant to prevent aggregate formation. It was not clear if the presence of such a chemical, specifically sodium tetradecyl sulphate (STS) had any effect on the surface properties or other properties of the spheres which might specifically result in or contribute to their efficacy. To decrease the number of variables involved, the Bi-link spheres in this experiment were prepared in the presence of STS, with or without fibrinogen, even though the novel method presented in this Invention does not require the presence of STS.

Also, U.S. Pat. No. 6,264,988 B1 disclosed a method of producing spheres by using various pumps to deliver the respective reagents through a silicone tubing system to critical mixing points for mixing. It was designed for production of massive amounts of sphere suspensions. The present experiment by contrast, achieved mixing of smaller quantities of reagents in rigid plastic tubes or glass flasks.

Materials and Methods: Both HSA 25% and human fibrinogen were purchased from Baxter Healthcare Corp. Glutaraldehyde (GL) was chased from Electron Microscopy Science (EM grade, Port Washington, Pa.) Sodium Tetradecyl sulphate (STS 27%, Niaprof 4, which is the same anionic surfactant formerly produced by Union Carbide under the Tergitol name) was purchased from Sigma, St. Louis.

To approximate as much as possible the concentration of reagents at the mixing junctions as the disclosed prior art of U.S. Pat. No. 6,264,988 B1 the following steps were used for the present experiment:
  (a) Preparation of 50 ml of albumin solution containing a detergent with the correct concentration of salt: To a 50 ml polypropylene tube 6.25 ml of water was first added, followed by 5 ml of STS (0.2 mg/ml diluted in water), followed by 3.75 ml of a ten-fold saline solution (90 mg of sodium chloride/ml) and finally 35 ml of Buminate (25%.) This solution contained the appropriate amount of STS and sodium chloride in the protein solution ready for use in the next step and was called snHSA.
    Therefore, the concentration of the constituents in snHSA (before addition of GL and other reagents) was as follows: HSA (17.5%); STS (0.02 mg/ml); added sodium chloride (6.75 mg/ml, not counting any cations or anions contributed from the stock 25%-HSA)
  (b) The sub-stabilizing concentration and the stabilizing concentration of GL were prepared by dilution with water a stock solution of GL (10%) to 0.1 mg/ml (50 ml prepared), and 12.5 mg/ml (10 ml prepared), respectively.
  (c) Ethanol was prepared by dilution with water to 70% in a 500 ml glass-flask: Because of the relatively large volume needed, the total volume was added to the protein solution in two equal aliquots, with thorough mixing in between to prevent local areas of high alcohol concentrations within part of the solution mixture.
  (d) Solutions of human fibrinogen (each 10 ml) were prepared by dilution of a stock fibrinogen solution (2%) with normal saline to achieve concentrations of 2.0, 1.75, and 1.5 mg/ml, respectively. This concentration refers to the concentration of fibrinogen in the solution before addition to the turbid sphere suspensions (added at a ratio of about 0.2 volume of fibrinogen solution per volume of turbid sphere suspension.)

Each of the above components was mixed thoroughly by shaking after each step at room temperature (19 C to 23 C acceptable.) The time indicated in each step was actual time following time zero, not the time-interval from the previous step. The step-by-step procedure of mixing was as follows:

For Preparation 7-A: (1) 6.2 ml of snHSA was removed from the stock solution and added to a sterile 50 ml polypropylene tube; (2) At time zero, 6.2 ml of the sub-stabilizing concentration of GL was added; (3) at 15 seconds, 10.5 ml of Ethanol (70%) as the desolvating agent was added; a slight turbid appearance could be observed in part of the solution which would quickly redissolve (or clarify) upon shaking of the polypropylene tube (because local high concentrations of alcohol was redistributed by the improved mixing); (4) at 30 seconds, another 10.5 ml of Ethanol (70%) was added; the suspension became completely and stably turbid; (5) at 2 minutes, 1.3 ml of the stabilizing concentration of GL was added; (6) at 5 minutes, 4.1 ml of 10-fold saline (90 mg sodium chloride/ml) was added to bring the suspension close to physiological isotonicity; (7) at 6.5 minutes, 8.3 ml of fibrinogen solution (2.0 mg/ml) was added.

For Preparation 7-B and Preparation 7-C: the above procedure was repeated, except the fibrinogen concentration was 1.75 and 1.50 mg/ml, respectively.

For Preparation 7-D which was the control sphere suspension (CS), step (7) was omitted.

After the 4 different sphere preparations were manufactured, they were dialyzed 3 times against at least 10 fold excess of distilled water to remove the desolvation agent, any dialyzable molecules and the detergent. An appropriate excipient comprising of maltose, lactose and glycine was added to facilitate storage by freezing at −18 degree C.

Results:

The concentration of spheres (in the samples after thawing the frozen preparations) in Preparation 7-A, 7-B, 7-C and 7-D were 4.6, 4.6, 3.0 and 7.1 mg of spheres per ml suspension, respectively; the amount of fibrinogen attached were 3.5, 2.7, 3.1 and zero ug of fibrinogen per mg sphere, respectively.

The average size of the spheres in all 4 preparations were similar, being about 0.8 micron in diameter and did not have any spheres or particles larger than 5 micron. The preparations all appeared homogeneous in size distribution.

Comments and Conclusions: The data showed that albumin spheres made in the presence of STS, with HSA from a supplier other than Alpha Therapeutics (in this case Baxter Healthcare Corp) using the novel Bi-Link method was capable of binding fibrinogen. Since the amount of fibrinogen bound was 3.1 ug/mg spheres when the fibrinogen solution used was 1.5 mg/ml, which was comparable to the 2.7 ug of fibrinogen bound per mg spheres when the fibrinogen solution used was 1.75 mg/ml, the data suggested that under these conditions of mixing, 1.5 mg of fibrinogen/ml might have reached a saturating concentration for use in coating the spheres in the present method.

The data suggested that useful spheres may also be produced by the novel Bi-link method without the addition of a detergent in the protein solution and that a fibrinogen solution can be added to such a sphere suspension. The suspension made with this novel method would not have any detectable amount of large spheres or particles (greater than 5 micron), in contrast to the suspensions made by the prior art method (using identical initial concentrations of reagents) which resulted in a sub-population of large spheres.

The data also showed that the desolvation agent could be added in two divided steps and still resulted in biologically useful and safe sphere suspensions.

EXPERIMENT 8

Evaluation of the Medical Efficacy of Albumin Spheres Coated with Fibrinogen and that of Control Spheres in Thrombocytopenic Rabbits Purpose: To evaluate the medical benefit of intravenous infusion of albumin spheres prepared by the Bi-Link method, comparing spheres coated with fibrinogen and those without fibrinogen (CS)

Rationale: Previous in vivo studies using thrombocytopenic rabbits to demonstrate efficacy in the improvement in bleeding time (BT) or bleeding volume (BV) involved spheres made with the Post-link method in the presence of a surfactant (STS). This experiment was design to evaluate if spheres prepared by the Bi-link method had similar efficacy.

To make spheres prepared by the Bi-link method as similar as possible to those made with the older disclosed Post-link method, the spheres in this experiment were prepared in the presence of STS, even though in this Invention the novel Bi-link method does not require the presence of any added surfactants or detergents. This was done in view of the fact that the effect of an added detergent or surfactant on the medical efficacy of the sphere was unknown. In case the Bi-link method produced spheres which did not shorten the Bleeding Time of thrombocytopenic rabbits, there would be one less confusing factor (that of the potential beneficial effect of a surfactant in the manufacturing step).

The data in this experiment showed that Bi-linked spheres prepared in the presence of a surfactant were effective in vivo. Subsequent experiments to be described below will show that the presence of a detergent in the protein solution was not a factor in the efficacy of the spheres prepared by this novel Bi-link method. Spheres prepared without the added surfactant or detergent in the protein solution were also effective in vivo.

Material and Methods:

The method of production of Bi-Link spheres was described in Experiment 7. Specifically, suspensions containing spheres with 3.5 ug fibrinogen/mg sphere (Preparation 7-A, with 4.6 mg spheres per ml suspension) and control spheres with no fibrinogen (Preparation 7-D with 7.1 mg spheres per ml suspension) were used for the in vivo studies here.

Method of using BT to evaluate various platelet substitute products was described in "Novel Platelet Products and Substitutes" by D. H. Lee and M. A. Blajchman (Transfusion Medicine Reviews, vol 12, No 3, July 1998, pp 175-187.) Rabbit platelet count was done by a manual method and was not affected by the protein spheres infused into the animals.

Results:

Table 8-1 showed the platelet counts (×10 billion/L) at various times and the BT (in seconds.) Rabbits that continued to bleed over 900 seconds had the wound compressed temporarily to stop the bleeding. Therefore BT over 900 seconds would be interpreted to indicate a lack of efficacy of the infused product.

All 6 rabbits received 6 ml of sphere suspension/kg weight, intravenously, to ensure equal volumes of fluid were infused.

Rabbits 1, 2, 3 were infused spheres with fibrinogen (Preparation 7-A) and Rabbits 4, 5, 6 were infused with control spheres (Preparation 7-D.)

TABLE 8-1

Platelet Counts of irradiated thrombocytopenic rabbits and their Bleeding Time at 1 hr and 24 hr post-infusion of spheres

| Rabbit # | Weight, kg | Platelet Ct, Pre-infusion | Platelet Ct, 0.5 hr post-infusion | Platelet Ct, 1 hr post-infusion | Platelet Ct, 24 hr post-infusion | Bleeding Time, 1 hr post-infusion | Bleeding Time, 24 hr post-infusion |
|---|---|---|---|---|---|---|---|
| 1 | 3 | 38 | 19 | 20 | 11 | 810 | 540 |
| 2 | 2.8 | 22 | 24 | 17 | 22 | >900 | 489 |
| 3 | 3.1 | 28 | 31 | 36 | 34 | 735 | >900 |
| 4 | 2.7 | 24 | 24 | 12 | 14 | >900 | >900 |
| 5 | 3 | 38 | 38 | 18 | 21 | 500 | 145 |
| 6 | 2.9 | 10 | 7 | 6 | 12 | 378 | 290 |

The data showed that the weight and platelet counts were comparable for the 6 rabbits, with Rabbit 6 being the most thrombocytopenic.

Rabbit 1 showed that Preparation 7-A clearly had efficacy lasting up to (and probably beyond) 24 hours after infusion of the fibrinogen-coated spheres. Rabbits 2 showed that what appeared to be an ineffective dose at 1 hour post-infusion was clearly effective by 24 hours. The reason for the delay was not clear. Efficacy might have taken place soon after 1 hour post-infusion but BT at such a time point (e.g. at the 4-hour time point) was not performed. Rabbit 3 showed that what was effective at 1 hour post-infusion at this dose was not observed at 24 hour post-infusion. Whether this observation was due to a relatively low dose (compared to the effective dose which needs to be determined) which could be improved was not clear from this experiment. But overall, the combined data from rabbit 1 to 3 showed that, as expected, spheres coated with fibrinogen in vitro as a part of the synthesis procedure, even when prepared by this new Bi-link method (but in the presence of STS) was effective.

The totally unexpected result was showed by Rabbit 5, and 6. While Rabbit 4 showed no efficacy at 1 hour and 24 hour post-transfusion of Preparation 7-D (spheres with no fibrinogen added in vitro) Rabbit 5 and 6 demonstrated clear efficacy of spheres without pre-coating of fibrinogen in vitro. Even though Rabbit 6 had the lowest platelet count pre-infusion, the improvement in BT was clearly the best (145 seconds at the 24-hour time point.) The effect of CS on Rabbit 5 and 6 lasted up to 24 hour and indeed appeared to have been even better at the 24 hour time point than the values at 1 hour.

Comments: There could be any number of hypotheses to explain why control spheres without fibrinogen added in vitro as part of the manufacturing procedure would show efficacy in vivo. One probably theory was that the control or blank spheres manufactured by the Bi-Link method were capable of capturing endogenous fibrinogen and/or other coagulation factors and/or other biological molecules, after entry into the circulation system.

The reason why previously prepared control Post-link spheres, using a different method of production (in accordance to disclosed prior art) failed to demonstrate efficacy in the same animal model was not clear. Since the present batch of Bi-link spheres was deliberately produced in the presence of a surfactant (even though the Invention does not require it) the difference in results was not due to the effect from the absence or presence of a surfactant or detergent in the protein solution.

Control spheres prepared by the Bi-link method have several advantages compared to spheres pre-coated in vitro with fibrinogen. (1) The steps involved in adding fibrinogen were eliminated, saving time and cost of material; (2) The animal or patient would supply a natural source of species-specific fibrinogen, or the active biological ingredient in the "activated device" and therefore avoid exposure to a source of foreign antigen from a different species.

Since commercial sources of species-specific serum albumin were more likely to be available than species-specific fibrinogen, or other useful biological molecules, spheres could be prepared with species-specific albumin for veterinarian applications, if needed, without the trouble of having to locate or prepare a species-specific fibrinogen source or a species-specific useful biological molecule.

Toxicology of spheres prepared by the Bi-link method was not performed here. But previous studies of the Post-link spheres demonstrated that the toxicity of Post-link sphere suspensions (containing spheres larger than 5 micron in diameter) could be removed by the elimination of large particles. Therefore, Bi-link spheres are expected to show improved toxicology profiles compared to those Post-link preparations containing large spheres.

EXPERIMENT 9

Comparing the Medical Efficacy of Control Spheres Prepared by the Novel Pre-link and Bi-link Method Purpose: To prepare four Control Sphere (CS) preparations with a size difference, using two methods, for evaluation of the products in their potential improvement in the Bleeding Time of thrombocytopenic rabbits, in vivo Rationale: Experiment 8 showed that CS produced by the Bi-Link method (Preparation 7-D) improved BT in thrombocytopenic rabbits. The present experiment aimed at producing spheres using again the Bi-link method, still in the presence of STS but aiming at 2 products, one about 1-2 micron ("medium-sized spheres") and another smaller than 1 micron in diameter ("small spheres"), to evaluate any difference in the efficacy due to the size of the spheres, in improving Bleeding Time (BT) in thrombocytopenic rabbits in vivo.

The size difference in spheres was controlled by the amount of sodium chloride added to the albumin solution before the resultant albumin solution was mixed with other non-protein solutions or reagents.

In addition, in this experiment, Pre-Link spheres were also prepared, again in the presence of an added surfactant, even though the novel Pre-link method of this Invention does not require the presence of a surfactant or detergent in the protein solution. To make it possible for comparison with the disclosed prior art (which resulted in Post-link sphere suspensions) the average size of the Pre-link spheres synthesized in this experiment was kept as close as possible to 1-2 micron (called "medium-sized spheres" here) and without any sub-population of large spheres.

Further refinements (by controlling the concentration of sodium chloride in the albumin solution) produced Pre-link spheres smaller than 1 micron in diameter (called "small spheres" here.)

All four sphere suspensions were evaluated in their efficacy in improving BT in thrombocytopenic rabbits in vivo.

Material and Methods:

Materials were obtained from the same suppliers as in Experiment 7; specifically, the 25% HSA used was Buminate from Baxter.

For the synthesis of "medium-size spheres" (1 to 2 microns) the "snHSA-M" solution was prepared as follows: (a) In a 50 ml polypropylene tube, 21.25 ml of water was added; (b) then 3.75 ml of a 10-fold saline (90 mg sodium chloride/ml) was added; (c) then 5 ml of STS (0.2 mg/ml) was added; (d) then 20 ml of a HSA-25% from supplier B was added. All the components were well mixed before aliquots were removed for use in synthesis of different spheres as described below.

Reagents were added at specified times from Time Zero which was the time of mixing of the "snHSA-M" with the first non-snHSA-M reagent. These time designations were not time intervals from the addition of the immediate preceding reagent.

For the Pre-link medium-size spheres (PMS): 6.27 ml of "snHSA-M" (described above) was added to a 50 ml polypropylene tube. Then at time zero 6.27 ml of GL (1.6 mg/ml in water) was added. At 15 seconds, 12 ml of ethanol (70% in water) was added. At 30 seconds, another 12 ml of ethanol (70% in water) was added. Then the turbid suspension was dialyzed in water to remove all diffusible molecules from the suspension. This preparation was designated as Preparation PMS.

For the Bi-link medium-sized spheres (BMS): 6.27 ml of "snHSA-M" (described above) was added to a 50 ml polypropylene tube. Then at time zero 6.27 ml of a sub-stabilizing concentration of GL (0.1 mg/ml in water) was added. At time 15 second, 12 ml of ethanol (70% in water) was added. At time 30 second, another 12 ml of ethanol (70% in water) was added. Then at time 2 minutes, a stabilizing concentration of GL (1.25 ml, 12.5 mg/ml in water) was added. Thereafter the turbid suspension was dialyzed in water. This preparation was designated as BMS.

Microscopy showed that there were no aggregates in both PMS and BMS preparations, nor spheres larger than 5 microns. The most common size in both preparations appeared to be about 2 to 3 micron in diameter.

For synthesis of small spheres (less than 1 micron) the "snHSA-S" solution was prepared as follows: (a) In a 50 ml polypropylene tube, 22.5 ml of water was added; (b) then 2.5 ml of a 10-fold saline (90 mg sodium chloride/ml) was added; (c) then 5 ml of STS (0.2 mg/ml) was added; (d) then 20 ml of a HSA-25% from supplier B was added. All the components were well mixed before aliquots were removed for further use in synthesis of small spheres to be described below. The difference between "snHSA-S" and "snHSA-M" was in the added sodium chloride content.

For the Pre-link small sphere (PSS) method: the same volume and steps were used as in the Pre-link medium-sized spheres (PMS) except that in place of the snHSA-M solution, the "snHSA-S" (as described immediately above) was used. This sphere suspension was designated as PSS.

For the Bi-link small sphere (BSS) method: the same volume and steps were used as in the Bi-link medium-sized spheres (BMS) except that in place of the snHSA-M solution, the "snHSA-S" (as described immediately above) was used. This sphere suspension was designated as BSS.

Microscopy showed that there were no aggregates in both PSS and BSS preparations, nor spheres larger than 5 micron. The most common sphere size appeared to be 0.8 micron, in both preparations.

Results:

The concentration of spheres in the PMS, BMS, PSS and BSS suspension (after addition of an appropriate excipient suitable for freezing the sample without causing aggregation of the spheres upon thawing) was found to be 3.3, 2.06, 4.46 and 2.53 mg/ml of the suspension, respectively, Again, 6 ml of each suspension per kg weight was infused into thrombocytopenic rabbits (to maintain the same degree of hydration by the infusion.)

Table 9-1 showed the improvement in Bleeding Time in thrombocytopenic rabbits after infusion of each preparation of spheres, all without pre-added or pre-coating of fibrinogen in vitro.

The Bleeding Time of thrombocytopenic rabbits which did not receive any infusion of spheres or which had only been infused with normal saline had historically been shown to be consistently over 900 seconds and therefore not repeated or reported in this experiment.

Rabbits 1, 2, 3 were transfused Preparation PMS (Pre-link medium spheres)

Rabbits 4, 5, 6 were transfused Preparation BMS (Bi-link medium spheres)

Rabbits 7, 8, 9 were transfused Preparation PSS (Pre-link small spheres)

Rabbits 10, 11, 12, 13 were transfused Preparation BSS (Bi-link small spheres)

Preparation PMS appeared to be the least efficacious of the 4 preparations. It was not clear if the lack of improvement in BT at the 1 hr and 24 hr time point was due to a delay of the on-set of efficacy as measured at one hour post-infusion, because Rabbit 1 showed a mild improvement at 24 hours (BT was 885 second.) An alternative explanation of the observation was a dosage effect in terms of the number of particles per ml. For example, the formula calculating the mass of a sphere 2.4 micron in diameter would indicate that it would have a mass 27 times the mass of another sphere which was 0.8 micron in diameter. Therefore even if the same dose in terms of mg sphere/kg was infused, the number of 2.4 micron spheres infused would be 27 times fewer than the number of 0.8 micron spheres infused.

In rabbits (number 4, 5, 6) infused with preparation BMS, one out of three rabbits showed improvement in BT as early as 1 hour. By 24 hours, all three showed efficacy. Rabbits infused with small spheres, e.g. Rabbit 7, 8, 9 (infused with PSS) all three rabbits showed no efficacy in 1 hour, but all three showed improvement by 24 hours post-infusion.

In rabbits infused with BSS, rabbit number 10, 11, 13 all showed efficacy in both the 1 hour time point as well as the 24 hour time-point. Again the results at the 24 hour time-point was even better than the results of BT at the 1 hour time-point, suggesting the effect of these spheres could last longer than 24 hours. It was not clear why Rabbit #12 did not show efficacy both at the 1 hour and the 24 hr time-point. Rabbit #12 did not have platelet count substantially less than the other three rabbits. In fact Rabbit 13 had the overall lowest platelet count but showed good improvements in BT at both the 1 hour and 24 hour time-point.

Conclusion: the control or blank spheres prepared with Bi-link method (regardless of size) again showed efficacy in improvement of BT, confirming the results of Experiment 8. Control or blank spheres prepared with the Pre-link method (regardless of size) also showed efficacy. These results were totally unexpected.

Although all four preparations in this experiment were manufactured in the presence of added surfactant in the protein solution, experiments to be described below showed that the spheres made in the absence of a surfactant or detergent could be also effective in thrombocytopenic rabbits, in vivo.

The thrombocytopenic rabbit model was highly reproducible and consistent between experiments. It is not clear at this

TABLE 9-1

Platelet count and Bleeding Time in thrombocytopenic rabbits

| Rabbit # | Wt, kg | Platelet Ct, Pre | Platelet Ct, 0.5 hr Post | Platelet Ct, 1 hr Post | Platelet Ct, 24 hr Post | Bleeding Time 1 hr Post | Bleeding Time 24 hr Post |
|---|---|---|---|---|---|---|---|
| 1 | 2.8 | 3 | 74 | 44 | 33 | >900 | 885 |
| 2 | 2.7 | 28 | 74 | 8 | 16 | >900 | >900 |
| 3 | 3 | 28 | 39 | 14 | 17 | >900 | >900 |
| 4 | 2.7 | 18 | 61 | 39 | 35 | >900 | 855 |
| 5 | 2.7 | 24 | 5 | 9 | 23 | 615 | 233 |
| 6 | 2.7 | 16 | 33 | 12 | 17 | >900 | 870 |
| 7 | 3.2 | 24 | 48 | 24 | 45 | >900 | 325 |
| 8 | 2.8 | 22 | 52 | 15 | 22 | >900 | 455 |
| 9 | 3 | 24 | 34 | 18 | 36 | >900 | 730 |
| 10 | 3.2 | 50 | 68 | 34 | 63 | 300 | 143 |
| 11 | 3.1 | 24 | 88 | 43 | 47 | 310 | 260 |
| 12 | 3.2 | 38 | 79 | 40 | 22 | >900 | >900 |
| 13 | 3 | 15 | 35 | 32 | 31 | 895 | 162 |

The data showed that all 13 rabbits were thrombocytopenic and had not recovered their platelet count as of 24 hour post-infusion.

time why the control spheres produced by the previously disclosed Post-link method did not result in improvement of BT in vivo (e.g. the "CS" in FIG. 6, of U.S. Pat. No. 6,264,988

B1) during the extensive period of their evaluation as experimental controls for fibrinogen-coated Post-link spheres (fibrinogen added in vitro as part of the synthesis method.)

The data here suggested there may be intrinsic differences in the properties of spheres prepared by the Post-link method in the prior art versus those prepared with the Pre-link and Bi-link method disclosed here.

It is expected that sphere suspensions produced with other kinds of albumin (such as recombinant albumin or modified albumin) or albumin obtained from other species, such as bovine or horse albumin, or directly from plasma obtained from various species without further isolation or purification, using the Bi-link or the Pre-link method, or other methods described in this disclosure, could be equally efficacious without pre-coating with fibrinogen in vitro before administration into the animals.

Regarding spheres prepared with the novel Mid-link method or any of the novel methods described in this Invention, it is also expected that those spheres could also bind fibrinogen or other useful biological molecules after administration in vivo and became efficacious in the improvement of BT in thrombocytopenic subjects (regardless of the etiology of platelet low count or dysfunction.)

EXPERIMENT 10

Preparation of Mid-link Spheres Without Added Surfactant and Evaluation of Their Efficacy in Thrombocytopenic Rabbits After Terminal Sterilization Purpose:

This experiment has several aims: (1) To see if small spheres can be prepared with the Mid-link method using HSA solutions purchased from Baxter. (2) To evaluate whether such spheres could withstand high pressures inside sealed plastic bottles as a method of terminal sterilization. (3) Whether such treatment affected the efficacy of these sphere suspensions prepared in the absence of surfactant, in the improvement of Bleeding Time in thrombocytopenic rabbits.

Rationale:

In all previous experiments evaluating the efficacy of sphere preparations, the sphere suspensions had always been prepared in the presence of an added surfactant (specifically STS) to make them easier for comparison to the thrombocytopenic rabbit data disclosed in the prior art. In this Invention, however, it was discovered that the new in vitro methods using all five approaches (novel Pre-link, novel Mid-link, novel Post-link, novel Bi-link and novel BiMid-link) did not require the presence of added surfactant and could result in suspensions without large spheres (greater than 5 micron) and without aggregation.

It could not be predicted from theory whether the presence or absence of an added surfactant to the in vitro manufacture method would have any in vivo effect. For example, if the surface of the spheres were to be denatured slightly during manufacture because of the presence or absence of a surfactant, the body might be inclined to remove such spheres by phagocytosis or by other physiological defenses, leading to diminished or lack of in vivo efficacy. Evaluation by infusion into thrombocytopenic rabbits in vivo remained the best method to evaluate whether spheres prepared by the novel methods in the absence of surfactants were efficacious.

Good manufacturing procedures would expect a "terminal sterilization" step where the contents inside a bottle would be subjected to sterilization after the seal had been secured. In the food industry, high pressure has been used to sterilize sea food without loss of taste and texture. See for example, "Effects of High Pressure on Texture and Microstructure of Sea Bass (*Dicentrarchus labrax* L.) Fillets" by R. Cheret, Journal of Food Science 70 (8), e477-e483.

Material and Method:

Preliminary experiments (not shown here) had demonstrated that a mixture of ethanol (ranging from 45% to 75% diluted from 100% ethanol with water) all containing a glutaraldehyde (GL) concentration of 0.5 mg GL/ml could be used to produce sphere suspension with any number of albumin concentrations (ranging from 3% to 18%) with the Mid-link method.

The sphere suspensions discussed in disclosed prior arts were produced only with 70% alcohol as a desolvation agent containing no GL within. In addition, in the prior art, the GL was to be added before, or after the addition of ethanol, in a separate step. So using ethanol solutions containing as low as 45% ethanol in the mixture was a novel approach. Furthermore, the inclusion of a crosslinking agent in the desolvation agent was innovative.

Any mixture of such ethanol solutions containing GL as a crosslinking agent (the mixture to be used as a desolvation agent in the Mid-link method) will be called EG, with a number following to indicate the concentration of the alcohol content. For example, EG70 will mean the concentration of ethanol is 70% (GL constant at 0.5 mg/ml.) It was found in preliminary experiments (not shown here) that the higher concentration of ethanol in the EG mixture to be used as the desolvation agent, the greater yield of spheres could be obtained from a given initial concentration of albumin solution (the concentration before the EG was added.) And a higher initial concentration of albumin (before the EG was added) will lead to a higher concentration of spheres in the suspension after the addition of the EG solution.

In this experiment the following steps were followed: (1) Buminate 25% was diluted with water (with no added surfactant or detergent) to result in 92.3 ml of a 5.5% solution; (2) to the 5.5% albumin solution, 307.7 ml of EG60 was added quickly to result in 400 ml of turbid sphere suspension.

The suspension was dialyzed in room temperature 3 times each against tenfold excess of water to remove any dialyzable molecules. On microscopic examination of the dialyzed suspension, fine particles (probably spheres) less than 0.1 micron were seen in a very dense population. The solids were too small to be visualized as individual spheres under the 1000-fold magnification phase-microscope.

An excipient was prepared by dissolving 27 gram of lactose, 27 gram of maltose and 12 gram of glycine (all purchased from Sigma) in 300 ml of water. The final volume after all the sugars and amino acids were dissolved exceeded 300 ml. The solution was filtered with a 0.2 micron filter before mixed one part by volume per 3 parts by volume of sphere suspension.

The concentration of the spheres (post-dialysis and post-excipient addition) was about 5 mg/ml.

Terminal Sterilization: After the sphere suspensions (containing excipient) were dispensed (10 ml) into the plastic bottles (made of polyolefin, a copolymer of ethylene and propylene, or any material such as the LifeShield Plastic Vials sold by Hospira, Inc, Lake Forest for their Sterile Water for Injection, USP) the gray butyl stoppers were placed tightly and an aluminum flip-off cap (purchased from Kimble) was applied. The bottles were pressurized using standard high pressure equipment such as those described in the literature. Starting temperature in the tank was 39 degree F., highest run temperature was 79 degree F. Extremely high hydrostatic pressure (600 MPa) was applied, average ramp-up time was about 2:12 minutes. Three consecutive runs of 1 minute each were done, with about 5 minutes in between each run to allow time to reset and rechill the tank water. The overall appearance to the unassisted eye of the sphere suspension inside the plastic bottle after pressure treatment did not change from before pressurization. Inspection under a phase microscope revealed no discernable change in size. There remained no aggregates or clumps in the suspension of spheres. At this high pressure of 600 MPa, it is expected all common bacteria and viruses would be killed.

After terminal sterilization, a portion of the plastic vials containing sphere suspensions were kept at room temperature, others at refrigeration temperature, and the rest were frozen at minus 18 degree C. All appeared to have no change by visual and microscopic inspection after storage for at least 7 months under the respective conditions.

The sphere suspension stored in room temperature was designated as Preparation 10-B.

Result:

Table 10-1 showed the improvement in Bleeding Time (BT) in thrombocytopenic rabbits after infusion with spheres that had been terminally sterilized in plastic vials and have been stored in room temperature (22 to 28 deg C.) for about 3.5 months (for rabbit 1, 2, 3) or for about 8 months (rabbit 21, 22, 23.) Essentially the rabbits were prepared by the same protocol and infused with 6 ml of the Preparation 10-B per kg weight of the rabbit. The concentration of spheres in Preparation 10-B was 4.6 mg/ml; so the dose was 27 mg of spheres/kg of rabbit weight.

appeared to be flexible enough to withstand the pressure, in 3 consecutive pulses. It was known that infectious agents not completely deactivated by one pulse of high pressure could be inactivated by repeated pulses. It was entirely unexpected that the spheres could maintain their shape and individuality without being squeezed together to form clumps or aggregates during the high pressure phase or release from it.

Preliminary experiment evaluating the effect of high pressure on the soluble coagulation factors showed that extreme high pressures had no effect on the biological activity of the molecules (Provisional Patent filed "Inactivation of Infectious Agents in Plasma by Extreme Pressure"). It is expected that spheres prepared by the novel methods disclosed here without the addition of surfactants or detergents could be pre-coated with any number or any combination of coagulation factors in vitro and then the combined product pressurized in vitro as a terminal sterilization step. Such a high pressure treatment would be expected to kill any number of pathogens introduced from any of the components or steps used to make the sphere suspensions.

The evaluation in thrombocytopenic rabbits showed that Preparation 10-B, prepared in the absence of surfactants and without the addition of fibrinogen in vitro, could improve their BT. Rabbit 1 and Rabbit 3 both did not show any improvements in 2 hours after infusion of Preparation 10-B, while Rabbit 2 showed obvious (though mild) improvement. This result could not be explained by the degree of platelet deficiency because Rabbit 3 had higher platelet counts than Rabbit 2.

TABLE 10-1

Platelet count (Plt Ct, billion per liter) and Bleeding Time (in seconds) in thrombocytopenic rabbits before ("pre") and after infusion ("post") of spheres that had been subjected to extreme high hydrostatic pressure for terminal sterilization

| rabbit | Weight (kg) | Plt Ct (pre) | Plt Ct (30 min, post) | Plt Ct (2 hr, post) | Plt Ct (24 hr, post) | BT (post 120 min) | BT (post 24 hr) | HCT % |
|---|---|---|---|---|---|---|---|---|
| 1 | 3 | 26 | 32 | 31 | 25 | >900 | 603 | 26.3 |
| 2 | 3.1 | 36 | 37 | 42 | 30 | 750 | 548 | 30.9 |
| 3 | 2.7 | 61 | 58 | 51 | 23 | >900 | 565 | 28.1 |
| 21 | 2.7 | 37 | 40 | 31 | 27 | 565 | 290 | 25 |
| 22 | 2.6 | 44 | 47 | 30 | 26 | >900 | 615 | 25 |
| 23 | 2.3 | 41 | 20 | 46 | 10 | >900 | 408 | 26 |

Comments:

In previous experience, any time a volume of ethanol (typically at 70% diluted with water and containing no GL or other crosslinking agent) was added to an albumin solution that exceeded a 2:1 ratio, there would be clumping and formation of large aggregates observable by the unaided eye. It was therefore surprising that in this experiment, by using a lower ethanol concentration (60% in this experiment) which also contained GL (0.5 mg/ml) the desolvation agent mixture could be added at 3.33 volume per one volume of the albumin solution.

Moreover, the resultant suspension contained spheres less than 0.1 micron in diameter and had no aggregates, clumps, large spheres or large particles.

In addition, these spheres were prepared without the addition of any surfactants or detergents in vitro as part of the manufacturing process. The spheres were not pre-coated in vitro with fibrinogen or other biological molecules known to be useful for coagulation or hemostasis.

It was expected that solid containers such as glass bottles would easily crack under the extreme high pressure for terminal sterilization. However, the plastic bottles used here Similarly for spheres stored for about 8 months in room temperature, infusion into rabbit 22 and 23 did not show efficacy within 2 hours, but all three rabbits (number 21, 22, 23) showed efficacy at the 24 hour time point.

Pre-infusion BTs were not done because hundreds of thrombocytopenic rabbits similarly treated (data not shown here) all had BT greater than 900 seconds.

At 24 post-infusion, all 6 rabbits showed improvement in BT. Again it should be noted that the results in 24 hour was better than those obtained in 2 hour post-infusion. The data suggested that the beneficial effect could last longer than 24 hours.

The improvement in BT at 24 hour could not be explained by recovery of the rabbit platelet counts at that time. All 6 rabbits were still thrombocytopenic. The hematocrit (HCT %) was done to make sure some rabbits were not more anemic than others since anemia might affect BT values. The hematocrit values for all 6 rabbits were comparable.

Although the preparation in this experiment was dialyzed to remove the alcohol and any other dialyzable molecules, it was fully expected that non-dialyzed sphere suspensions could be treated in containers with a similar method of high pressure to achieve terminal sterilization. In case removal of a component of the sphere suspension, e.g. the desolvation agent, is preferred before terminal sterilization, any number of methods can be used, including hollow fiber dialysis units, reverse osmosis, filtering, centrifugation.

Conclusion:

Sphere suspensions could be prepared in the absence of added surfactant and in the absence of added fibrinogen in vitro. A desolvation agent containing ethanol and a crosslinking agent could be added at a ratio of more than 2 volumes per one volume of albumin solution as described in this experiment.

Spheres could be subjected to extreme high hydrostatic pressure (up to 600 MPa) in single or repeated pulses without disintegration, aggregation or any detectable change in properties. These spheres were efficacious in improving the BT in thrombocytopenic rabbits particularly after 2 hours post-infusion.

Spheres treated by high pressure could be stored in room temperature for at least 8 months without loss of efficacy in vivo.

It is expected that spheres prepared by all five novel methods (Pre-link, Post-link, Mid-link, Bi-link, BiMid-link) all in the absence of added surfactants or detergent and all without added fibrinogen in vitro can withstand extremely high pressures in single or repeated pulses to inactivate infectious agents without harm to the spheres or their effectiveness in vivo.

EXPERIMENT 11

Ultra-small Spheres Manufactured by the Mid-link Method Using Dialyzed Human Serum Albumin Solutions Purpose:

One question after evaluation of various sphere preparations in the thrombocytopenic rabbit model was the dosage effect, i.e. whether increasing the dose infused (without overhydration of the animal) will further improve the Bleeding Time. It is therefore desirable to prepare sphere suspensions with high concentrations of spheres (mg/ml).

In the disclosed prior art, it was pointed out that dialyzed samples of albumin had less tendency of forming aggregates. However, during dialysis of the 25% HSA, the oncotic pressure of the albumin would draw water into the dialysis bag and therefore dilute substantially the concentration of the HSA. It was one aim of this experiment to dialyze the 25% HSA with external pressure against the dialysis bag to reduce as much as possible water intake into the dialysis bag, so that the resultant HSA solution would still be relatively high in concentration.

Such a high initial concentration of dialyzed albumin solution could allow supplementation of a small amount of sodium chloride for the purpose of controlling the average size of the spheres produced. The resultant concentration of spheres (mg/ml) would also be expected to be elevated compared to suspensions prepared by a low initial concentration of albumin solutions.

Material and Method:

25% Buminate (20 ml) were added to washed sterile dialysis tubings (Sigma D9652.) After the bags were tied, the entire bag was squeezed by two metal plates held under pressure with a C-clamp to counter the inflow of water, and dialyzed over time against distilled water. Preliminary data showed that dialysis against 25 fold excess water for about 3.5 hours resulted in essentially a complete removal of all chloride ions from the protein solution and less than 30 mEq of sodium ion left. Post-dialysis concentration of the HSA solution was 22.7%.

EG60 was prepared by dilution of 100% ethanol with water to 60% and adding enough GL to a final concentration of GL at 0.5 mg/ml.

The 22.7% dialyzed HSA solution was mixed without further dilution with various volumes of EG60. No surfactants or detergents were added.

Alternatively, lower concentrations of HSA solutions were prepared by dilution of the 22.7% solution with water, without the addition of surfactants or detergents.

The resultant suspensions were observed under phase microscope to evaluate the most common size distribution.

Result:

Table 11 showed the result of mixing 100 microliter of HSA at various concentrations (ranging from 22.7% to 15%) with various volumes of EG60.

Initially the 22.7% HSA solution (100 uL aliquots) was used directly to mix with increasing volumes of EG60. The data (tube 1 to 5) showed that spheres ranging from 1 micron to 0.1 micron in diameter could be obtained, all without aggregation or containing large spheres of greater than 5 micron in diameter. The yield was above 68.8% in these tubes and sphere concentration ranged from 25.7 mg/ml to 14.5 mg/ml.

Preliminary data (not shown here) had indicated that when a suboptimal amount of desolvation agent was added to the protein solution, the suspension contained a low concentration of spheres. However, when the ideal (peak) ratio was exceeded, the additional volume of desolvation agent did not increase the formation of spheres, but merely served to dilute whatever maximal amount of spheres could be generated under those conditions. The data presented in Table 11 suggested that yield of spheres from soluble albumin molecules had reached a high plateau and could not be raised by adding more than 5 parts of EG60 per one part of the 22.7% albumin solution (as in tube 1.) Adding more EG60 at ratios higher than 5 (i.e. more than 5 volumes of EG60 per one volume of 22.7% albumin) would in fact result in a more diluted suspensions of spheres (due to the large volume of EG added to the suspension).

TABLE 11

Results from mixing dialyzed chloride-free and low sodium albumin solutions with various volumes of desolvation agent containing crosslinking agent.

| Tube | Initial Concentration of HSA solution (%) | Vol of EG60 used (uL) | Most Common Size of spheres | Concentration of spheres, mg/ml | Yield, % |
| --- | --- | --- | --- | --- | --- |
| 1 | 22.7 | 500 | 0.5 to 1 | 25.7 | 73.2 |
| 2 | 22.7 | 600 | 0.3 | 20.6 | 68.2 |
| 3 | 22.7 | 700 | 0.1 to 0.2 | 19.2 | 72.7 |
| 4 | 22.7 | 800 | 0.1-0.2 | 17.1 | 73.1 |
| 5 | 22.7 | 900 | 0.1-0.2 | 14.5 | 68.8 |
| 6 | 21 | 700 | 0.3 | 16.5 | 67.5 |
| 7 | 20 | 700 | 0.2 to 0.3 | 15.6 | 66.9 |
| 8 | 19 | 700 | 0.2 | 13.6 | 61.7 |
| 9 | 18 | 700 | 0.2 | 12.2 | 58.3 |
| 10 | 17 | 700 | 0.1 | 11.3 | 57 |
| 11 | 16 | 700 | 0.1 | 10.3 | 55.3 |
| 12 | 15 | 700 | <0.1 | 9.1 | 52.2 |
| 13 | 18 | 800 | 0.2 | 10.9 | 58.4 |
| 14 | 18 | 900 | 0.2 | 10.3 | 61.7 |
| 15 | 18 | 1000 | 0.2 | 9 | 59.3 |
| 16 | 17 | 800 | <0.1 | 10.6 | 60.4 |

TABLE 11-continued

Results from mixing dialyzed chloride-free and low sodium albumin solutions with various volumes of desolvation agent containing crosslinking agent.

| Tube | Initial Concentration of HSA solution (%) | Vol of EG60 used (uL) | Most Common Size of spheres | Concentration of spheres, mg/ml | Yield, % |
|---|---|---|---|---|---|
| 17 | 17 | 900 | <0.1 | 9.2 | 58.2 |
| 18 | 17 | 1000 | <0.1 | 8.5 | 59.2 |

When a progressively lower concentration of HSA solution (ranging from 21% to 15%, from tube 6 to tube 12, respectively) was mixed with a constant volume ratio of EG60, the following were observed. Higher (initial) concentrations of protein solution produced comparatively larger spheres (tube 6 resulted in spheres of about 0.3 micron in diameter, as compared to tube 12 containing spheres barely visible, about <0.1 micron in diameter.)

The concentration of spheres obtained also was progressively lower as the initial concentration of the protein solution (before addition of EG60) was lowered. For example, starting with a concentration of 21% in tube 6, the final concentration of spheres was 16.5 mg/ml, as compared to that of tube 12, with initial concentration of protein being 15% which resulted in a concentration of spheres of 9.1 mg/ml.

Tube 13, 14, 15 started with albumin solutions of 18% which were rmixed, respectively with 800, 900 and 1000 uL of EG60. Again, a larger volume of EG60 used under these conditions resulted in a more diluted suspension of spheres, ranging from 10.9 to 9.0 mg/ml, in tube 13 and 15, respectively.

Tube 16, 17, 18 started with albumin solutions of 17% which were mixed, respectively with 800, 900 and 1000 uL of EG60. Again a larger volume of EG60 resulted in more diluted suspensions of spheres. It is particularly interesting to note that spheres in tube 13 to 15 were about 0.2 micron in diameter, but those in tube 16 to 18 were noticeably smaller, even though the difference in the initial concentration of albumin was only 1% in difference (17% in tube 16 to 18, as compared to 18% in tube 13 to 15.)

Comments:

High concentrations of dialyzed albumins solutions (e.g. a 22.7% albumin with essentially no chloride and only 30 milliequivalence of sodium) can tolerate high volumes of desolvation agents. For example, 9 volumes of EG60 could be added to one volume of this concentration of albumin (i.e. tube 5) without the formation of aggregates. In fact, a high concentration of small spheres, about 0.1 to 0.2 micron, was formed in suspension.

When a smaller ratio of desolvation agent to albumin solution (volume per volume) was used (e.g. in tube 1) the result was not simply a higher concentration of spheres (25.7 mg/ml, as compared to 14.5 mg/ml of spheres in tube 5.) The spheres were larger (0.5 to 1 micron in tube 1.)

The size of spheres produced by using dialyzed HSA solutions less than 18% in initial concentration (before addition of EG60) became very small and difficult to visualize in even a 1000× phase microscopy. But the suspension remains turbid, indicating that solid particles were present.

All of the above sphere suspensions were successfully prepared without the addition of surfactants or detergents to the protein solution before addition of the desolvation agent as described.

EXPERIMENT 12

Characterization of Ultra-small Sphere Suspensions Produced by Dialyzed Albumin Solutions in the Absence of Surfactants and Their Efficacy in Thrombocytopenic Rabbits Purpose:

(1) To characterize the property of a suspension produced by the novel Mid-link method from dialyzed albumin solutions, (2) To evaluate if such a suspension would improve the Bleeding Time in Thrombocytopenic rabbits.

Rationale:

The sphere suspensions produced by the prior art (using a Post-link method involving the presence of added surfactant) showed that several fractions of spheres were present. FIGS. 12A and 12B of U.S. Pat. No. 6,264,988 B1 showed, respectively, an ultra-small-size fraction of spheres, 0.25 to 0.3 micron in diameter, and another fraction around 0.8 micron in diameter. In addition, FIG. 12D disclosed a fraction of large spheres (about 3 to 4 micron and larger) which needed to be removed for safety reasons. It is therefore of interest to evaluate if suspensions produced by the novel Mid-link method contained single populations or multiple fractions of sphere sizes. It is of additional interest whether the ultra-small spheres produced by the Mid-link method were efficacious in thrombocytopenic rabbits.

Material and Methods:

Buminate 25% was dialyzed as described in Experiment 11. The dialyzed albumin solution was diluted with water to 18% without the addition of any surfactants. EG60 (44 ml) was mixed with 6.3 ml of the 18% albumin solution in room temperature (about 21 deg C.) Phase microscopy showed that the suspension contained very small spheres and no aggregates or irregular particles. An excipient was added (10 ml of LMG was added per 40 ml of suspension; LMG being 9%, 9%, 4% of lactose, maltose, glycine by weight added to water, respectively, as described.) The alcohol in the suspension was not removed.

A sample was sent to Microtrac Application Lab (Largo, Fla.) for evaluation with their dynamic light scattering technology. The remainder of the suspension was used in thrombocytopenic rabbits as described.

Results:

The size distribution of spheres in Preparation 100106-C was as follows:

TABLE 12-1

Tabulation of size distribution of spheres in Preparation 100106C

| Size (um) | % Chan | % Pass |
|---|---|---|
| 6.54 | 0.00 | 100.00 |
| 6.00 | 0.00 | 100.00 |
| 5.50 | 0.00 | 100.00 |
| 5.04 | 0.00 | 100.00 |
| 4.62 | 0.00 | 100.00 |
| 4.24 | 0.00 | 100.00 |
| 3.89 | 0.00 | 100.00 |
| 3.57 | 0.00 | 100.00 |
| 3.27 | 0.00 | 100.00 |
| 2.999 | 0.00 | 100.00 |
| 2.750 | 0.00 | 100.00 |
| 2.522 | 0.00 | 100.00 |
| 2.311 | 0.00 | 100.00 |
| 2.120 | 0.00 | 100.00 |
| 1.944 | 0.00 | 100.00 |
| 1.783 | 0.00 | 100.00 |

TABLE 12-1-continued

Tabulation of size distribution of spheres in Preparation 100106C

| Size (um) | % Chan | % Pass |
|---|---|---|
| 1.635 | 0.00 | 100.00 |
| 1.499 | 0.00 | 100.00 |
| 1.375 | 0.00 | 100.00 |
| 1.261 | 0.00 | 100.00 |
| 1.156 | 0.00 | 100.00 |
| 1.060 | 0.00 | 100.00 |
| 0.972 | 0.10 | 100.00 |
| 0.891 | 0.40 | 99.90 |
| .818 | 1.07 | 99.50 |
| 0.750 | 1.95 | 98.43 |
| 0.687 | 3.14 | 96.48 |
| 0.630 | 4.49 | 93.34 |
| 0.578 | 6.00 | 88.85 |
| 0.530 | 7.28 | 82.85 |
| 0.486 | 8.29 | 75.57 |
| 0.446 | 8.99 | 67.28 |
| 0.409 | 9.35 | 58.29 |
| 0.375 | 9.28 | 48.94 |
| 0.344 | 8.80 | 39.66 |
| 0.315 | 7.93 | 30.86 |
| 0.2890 | 6.70 | 22.93 |
| 0.2650 | 5.38 | 16.23 |
| 0.2430 | 3.99 | 10.85 |
| 0.2229 | 2.85 | 6.86 |
| 0.2044 | 1.94 | 4.01 |
| 0.1874 | 1.21 | 2.07 |
| 0.1719 | 0.61 | 0.86 |
| 0.1576 | 0.25 | 0.25 |
| 0.1445 | 0.00 | 0.00 |
| 0.1325 | 0.00 | 0.00 |
| 0.1215 | 0.00 | 0.00 |
| 0.1114 | 0.00 | 0.00 |
| 0.1022 | 0.00 | 0.00 |
| 0.0937 | 0.00 | 0.00 |
| 0.0859 | 0.00 | 0.00 |
| 0.0788 | 0.00 | 0.00 |
| 0.0723 | 0.00 | 0.00 |
| 0.0663 | 0.00 | 0.00 |
| 0.0608 | 0.00 | 0.00 |
| 0.0557 | 0.00 | 0.00 |
| 0.0511 | 0.00 | 0.00 |
| 0.0469 | 0.00 | 0.00 |
| 0.0430 | 0.00 | 0.00 |
| 0.0394 | 0.00 | 0.00 |
| 0.0361 | 0.00 | 0.00 |
| 0.0331 | 0.00 | 0.00 |
| 0.0304 | 0.00 | 0.00 |
| 0.02786 | 0.00 | 0.00 |
| 0.02555 | 0.00 | 0.00 |
| 0.02343 | 0.00 | 0.00 |
| 0.02148 | 0.00 | 0.00 |
| 0.01970 | 0.00 | 0.00 |
| 0.01806 | 0.00 | 0.00 |
| 0.01657 | 0.00 | 0.00 |
| 0.01519 | 0.00 | 0.00 |
| 0.01393 | 0.00 | 0.00 |
| 0.01277 | 0.00 | 0.00 |
| 0.01171 | 0.00 | 0.00 |
| 0.01074 | 0.00 | 0.00 |
| 0.00985 | 0.00 | 0.00 |
| 0.00903 | 0.00 | 0.00 |
| 0.00828 | 0.00 | 0.00 |
| 0.00760 | 0.00 | 0.00 |
| 0.00696 | 0.00 | 0.00 |
| 0.00639 | 0.00 | 0.00 |
| 0.00586 | 0.00 | 0.00 |
| 0.00537 | 0.00 | 0.00 |
| 0.00492 | 0.00 | 0.00 |
| 0.00452 | 0.00 | 0.00 |
| 0.00414 | 0.00 | 0.00 |
| 0.00380 | 0.00 | 0.00 |
| 0.00348 | 0.00 | 0.00 |
| 0.00319 | 0.00 | 0.00 |
| 0.00293 | 0.00 | 0.00 |
| 0.00269 | 0.00 | 0.00 |
| 0.00246 | 0.00 | 0.00 |
| 0.00226 | 0.00 | 0.00 |
| 0.00207 | 0.00 | 0.00 |
| 0.00190 | 0.00 | 0.00 |
| 0.00174 | 0.00 | 0.00 |
| 0.00160 | 0.00 | 0.00 |
| 0.00146 | 0.00 | 0.00 |
| 0.00134 | 0.00 | 0.00 |
| 0.00123 | 0.00 | 0.00 |
| 0.00113 | 0.00 | 0.00 |
| 0.00104 | 0.00 | 0.00 |
| 0.00095 | 0.00 | 0.00 |
| 0.00087 | 0.00 | 0.00 |

A summary was as follows:

| Data item | value | % Tile | Size (um) |
|---|---|---|---|
| MV (um) | 0.399 | 10.00 | 0.2389 |
| MN (um) | 0.2831 | 20.00 | 0.2788 |
| MA (um) | 0.355 | 30.00 | 0.312 |
| cs | 16.89 | 40.00 | 0.345 |
| sd | 0.1373 | 50.00 | 0.379 |
| MW | 1.71E+10 | 60.00 | 0.416 |
| Mz | 0.394 | 70.00 | 0.458 |
| ai | 0.1362 | 80.00 | 0.512 |
| Ski | 0.2074 | 90.00 | 0.590 |
| Kg | 0.977 | 100.00 | 0.657 |

MV means: Mean diameter in microns of the "volume distribution" represents the center of gravity of the distribution.
MN means: Mean diameter in microns of the "number distribution" is calculated using the volume distribution data and is weighted to the smaller particles in the distribution. This type of average is related to population or counting of particles
MA means: Mean diameter in microns of the "area distribution" is calculated from the volume distribution.
CS Means: Calculated Surface, provided in units of M squared/cc. The CS computation assumes smooth, solid, spherical particles.
SD means: Standard Deviation in microns.
Mz means: Graphic Mean which provides a less coarse-particle weighted mean particle size than MV. While it includes the median value, it can provide a different possibly better control value since both small and large particles are included in the calculation.
Ai means: Inclusive Graphic Standard Deviation. It includes more than 90% of the distribution and includes tails of distributions. The SD only includes 67% of the distribution.
Ski means: Inclusive Graphic Skewness. Skewness is a measure of how asymmetrical a curve is and how it varies from a normal, bell-shaped distribution. Ski includes 90% of the distribution and includes the "tails" of the distribution. A symmetrical curve has a Ski value of 0.00. Values of 1.00 to 0.30 show fine particles influencing the skew. Values of −0.30 to −1.00 show coarse particles as influencing the skew.
Kg means: Kurtosis (peakedness) Peakedness refers to "how sharp" a peak is. The peak is described as "Mesokurtic" if the value is between 0.90 and 1.11

In short, dynamic light scattering showed that the suspension consisted of one population of spheres, with an almost symmetrical distribution, the smallest detectable spheres being greater than 0.1576 micron and no spheres larger than 0.972 micron was present. The mean diameter (by number of distribution) was 0.2831 micron, with a standard of deviation of 0.1373.

Of importance is that the method can detect particles as large as 6.54 micron. Over the entire range from 1.060 to 6.54 micron, no particle within that size range was present in the suspension. This showed a great improvement of this Midlink method over the prior art in term of not having particles that can cause capillary obstructions in vivo.

The concentration of spheres was about 10 mg/ml in a suspension containing an excipient of sugars and amino-acids to render the suspension oncotically compatible with blood.

The efficacy of Preparation 100106C in thrombocytopenic rabbits was showed in Table 12-2. (Rabbit 4, 5, 6 were infused 3 ml suspension/kg; rabbit 7, 8, 9 had 1 ml/kg; rabbits 10, 11, 12 had 0.3 ml/kg.)

| Rabbit | Wt, kg | Plt Ct Pre | Plt Ct 0.5 hr post | Plt Ct 2 hr post | Plt Ct 24 hr post | BT 2 hr post | BT 24 hr post | HCT % |
|---|---|---|---|---|---|---|---|---|
| 4 | 2.7 | 55 | 52 | 60 | 21 | >900 | 425 | 32 |
| 5 | 2.8 | 53 | 2 | 8 | 32 | >900 | 360 | 31.9 |
| 6 | 2.8 | 37 | 12 | 19 | 38 | >900 | 668 | 27.5 |
| 7 | 2.7 | 24 | 27 | 24 | 17 | >900 | >900 | 30.1 |
| 8 | 2.9 | 47 | 35 | 37 | 30 | 428 | 320 | 27.5 |
| 9 | 3 | 46 | 46 | 43 | 56 | 306 | 248 | 27.3 |
| 10 | 3 | 50 | 41 | 40 | 23 | 325 | 725 | 29.9 |
| 11 | 2.9 | 51 | 59 | 60 | 70 | 285 | 227 | 30 |
| 12 | 2.9 | 47 | 28 | 49 | 47 | 455 | 460 | 24.3 |

Comments:

The in vivo data showed that spheres produced by the Mid-link method in the absence of added surfactant and without the addition of fibrinogen in vitro had a monodisperse distribution, mean diameter was about 0.3 micron.

These spheres were effective in improving the BT of thrombocytopenic rabbits. Of interest is the observation that the rabbits (number 4, 5, 6) which received the highest dose of spheres (30 mg per kg) appeared to have the least benefit at 2 hour post-infusion. But there was marked improvement at the 24 hour time point.

A medium dose of 10 mg/kg (to rabbits 7, 8, 9) resulted in two rabbits out of three that had improved BT. It was not clear why rabbit number 7 did not show improvement in its BT after one dose of these spheres.

A small dose of 3 mg/kg (to rabbits 10, 11, 12) by contrast had the highest efficacy. These rabbits showed improvements in both the 2 hour and the 24 hour time point post-infusion. The data suggested that the beneficial time may last longer than 24 hours.

EXPERIMENT 13

Spontaneous Binding of Fibrinogen In Vitro by Ultra-small Spheres After Prolong Storage in Room Temperature Purpose:

(1) To provide insight why ultra-small spheres without added fibrinogen in vitro could have a beneficial medical effect after infusion into thrombocytopenic rabbits. (2) To evaluate if Preparation 100106C could bind fibrinogen molecules in vitro without further use of crosslinking agents after prolong storage in room temperature.

Rationale:

In the prior art, for protein spheres to be efficacious in improving the Bleeding Time of thrombocytopenic rabbits, the spheres had to be coated in vitro with fibrinogen molecules. Those spheres were prepared by the Post-Link method and involved the presence of added surfactants in vitro during the manufacturing process.

Experiment 8, 9, 10, 12 showed that spheres prepared by the novel methods of "Pre-link", "Mid-link" and "Bi-link" all produced in the absence of surfactant and without added fibrinogen in vitro could improve the BT of thrombocytopenic rabbits. One theory would involve spontaneous binding or capturing of endogenous fibrinogen molecules or other useful molecules from the animal's plasma after infusion of these protein devices into the host.

One aim of this experiment was to evaluate if spheres made by one of these methods (Mid-link, Preparation 100106C) could bind fibrinogen molecules when exposed to plasma in vitro, without any involvement of crosslinking agents.

Experiment 6 and 7 already demonstrated the ability of Pre-link and Bi-link spheres to bind coagulation proteins.

Method:

Sphere suspension (Preparation 100106C) which had been prepared 20 days earlier was used in this experiment. Due to the small size of the spheres, they remained in suspension and did not sediment during this period of storage in room temperature. This aliquot contained alcohol as described in Expt 12 and had not been added any excipient. Plasma was obtained from a healthy donor with no exposure to anticoagulants. The plasma was diluted to several concentrations with normal saline, containing 1.2, 0.6, 0.3 mg fibrinogen per ml, designated as fibrinogen solution A, B, C, respectively. Solution D was normal saline serving as control.

Aliquots of Preparation 100106C (each 100 uL, after storage in room temperature for 20 days) was mixed with 400 uL of Fibrinogen solution A, B, C and control solution D. After one hour exposure in room temperature, the spheres, designated respectively as Preparation 13-A, 13-B, 13-C and 13-D were collected by repeated centrifugation and washing in normal saline to remove soluble proteins.

The concentration of spheres (mg/ml) was measured with the Pierce BCA method and the amount of bound fibrinogen on the spheres was evaluated with the Competitive ImmunoAssay as described in previous experiments.

The supernatant in the last washing was included in the fibrinogen assay and found to contain negligible concentrations of fibrinogen.

The concentration of fibrinogen bound to Preparation 13-A, 13-B and 13-C spheres were as follows: 0.85, 0.85, 0.72 ug fibrinogen per mg sphere. Control spheres exposed to only normal saline had no bound fibrinogen.

Comments:

The data showed that ultra-small spheres prepared by the Mid-link method, 20 days after synthesis were capable of spontaneous binding of fibrinogen from human plasma.

A comparison of the amount of fibrinogen bound per mg sphere showed that the binding capacity of these spheres for fibrinogen might have reached saturation at about 0.85 ug fibrinogen per mg sphere.

To assess if the spheres had the capacity to concentration fibrinogen from a diluted sample of plasma, the following calculations were done. The purpose was to calculate the amount of fibrinogen expected in diluted plasma in one average sphere volume and compare that with the amount of fibrinogen bound onto an average sphere from this dilute plasma fraction.

Using the size (sphere diameter) distribution tabulated in table 12-1, it could be calculated that the average volume of a single sphere in that population is $5.2 \times 10[-14]$ ml. In this volume, if the plasma concentration of fibrinogen was 0.3 mg/ml, the mass of fibrinogen would be $1.56 \times 10[-11]$ microgram.

To estimate the number of spheres represented by one mg of sphere mass, the following assumptions were made. Since the spheres did not settle for 20 days in room temperature undisturbed, the density could not be substantially different from one gram per ml. The weight of a single (average) sphere would be $5.2 \times 10[-11]$ mg. Each mg would contain $0.19 \times 10[11]$ spheres.

Since the spheres in Preparation 13-C was able to capture 0.72 microgram fibrinogen per $0.19 \times 10[11]$ spheres, the amount of fibrinogen captured in one sphere (average) volume was 3.8×10[−11] microgram of fibrinogen. This value is more than double the mass of fibrinogen expected in a similar volume of the diluted plasma. Therefore these spheres had the capacity of capturing and concentrating fibrinogen molecules from dilute samples of plasma.

The concentrating effect is possible because the albumin spheres probably have internal structures resembling a sponge, with connecting channels allowing passageway from the surface to the interior of the sphere. Albumin molecules both on the surface and the interior of the sphere formed scaffolds providing plenty of surfaces for the adhesion or adsorption of fibrinogen molecules.

The above calculation also suggested that in patients who had normal fibrinogen concentrations (determined to be 1.77 to 3.75 mg/ml) there was more than enough fibrinogen to fully saturate the binding capacity of the spheres.

The data from this experiment did not provide the lowest amount of fibrinogen bound per mg sphere which could still be efficacious. However, if 0.72 microgram of fibrinogen could be extracted from a severely hypo-fibrinogenemic solution, the data suggested that even in the hypo-fibrinogenemic patient, these spheres should still be effective for treatment of bleeding due to thrombocytopenia.

EXPERIMENT 14

Ultra-small Spheres Subjected to Terminal Sterilization by Heat and Their Efficacy in Thrombocytopenic Rabbits Purpose:
(1) to evaluate a second method of terminal sterilization, namely by heat, (2) and to evaluate if these treated spheres still have efficacy in the treatment of thrombocytopenic rabbits Rationale:
The spheres treated with extreme high pressure in Experiment 10 were dialyzed -to remove the alcohol and any other dialyzable molecules before filling into the plastic bottles for terminal sterilization by pressure. It may be advantageous to have a second method of terminal sterilization on suspensions containing alcohol, which may be better stored in glass bottles. Heating at 60 degree C. for 10 hours in the presence of stabilizers had been used as a method of terminal sterilization with human serum albumin solutions. We expect heating from room temperature up to 60 degree C. for up to or more than 10 hours will be effective for terminal sterilization of the biologic device.

Material and Method:
Ultra small spheres were prepared using a tubing system essentially similar to that described in U.S. Pat. No. 6,013,285 ("Large Scale Production Process with Instantaneous Mixing and Control Properties) and U.S. Pat. No. 5,716,643 (Large Scale Production of Medicine Coated Crosslinked Protein Microspheres) except for the following: (1) the Method used here was the novel Mid-link Method (not the Post-link.) Therefore the albumin solution was simply diluted from the 25% albumin solution (Buminate) with water without the addition of any surfactants or detergents and filled into the "HSA" bag via a 0.2 micron filter; (2) the crosslinking agent (glutaraldehyde at a final concentration of 0.5 mg/ml) was premixed with the ethanol (60%) and the mixture (EG60) was place in the second Bag, called the EG Bag here (corresponding to the Ethanol Bag in the disclosed prior art.) There was no GL or Fibrinogen bag in these experiments.

The pH of the 10% albumin solution was 7.0 plus or minus 0.5.

The pump rate for the albumin (10%) solution was 43 ml per min; the pump rate for the EG60 solution was 516 ml per min. Immediately after the two ingredients met at the junction, a static mixer was present inside the outlet tubing to thoroughly mix the two before the product was filled into the Product bag. The experiment was done at room temperature, essentially at 21 deg C. plus or minus 2 deg Centigrade.

The sphere suspension was first diluted with water to become 5.33 mg sphere per ml and than mixed in a 3 vol per 1 vol of excipient to contain 4 mg spheres/ml. Each pre-cleaned and sterile 50 ml-capacity (Wheaton) glass bottle was filled with 50 ml of the sphere suspension. The excipient was either (a) LMG prepared by dissolving 36 gram of Lactose, 36 gram of Maltose and 16 gram of Glycine in 400 ml of water; or (b) a dextrose solution prepared by dissolving 22 gram of dextrose in 100 ml of water. The final alcohol concentration in the excipient containing suspension was calculated to be about 31.1%.

Terminal Sterilization by heat was done by immersing bottles of spheres (in the dextrose excipient) in 60 degree C. water up to the neck of the bottles for 10 hours. The temperature of the water bath did not vary for more than plus or minus 0.5 degree C. for the duration. The suspensions looked slightly more yellow after the heat treatment with no gross precipitation or microscopic changes. No additional stabilizer (e.g. caprylate or acetyltryptophan) was added since the commercial Buminate 25% already had the appropriate stabilizer to albumin ratio and no dialysis was done to this sphere preparation that could have removed any stabilizer.

Thrombocytopenic rabbits were infused with various doses of spheres as follows: rabbits 24, 25, 26 (4 mg of non-heat-treated spheres/kg); rabbits 27, 28, 29 (1.3 mg of non-heat-treated spheres/kg.) Non-heat-treated sphere suspensions had the LMG excipient. Rabbits 30, 31, 32 were infused with 4 mg of heat-treated spheres per kg weight of the rabbits; these sphere suspensions had the dextrose excipient.

Results:
Microscopic examination of the sphere suspension before and after heat treatment revealed spheres of about 0.2 micron or less in diameter, no aggregates and no particles or spheres larger than 5 micron in the suspension. The suspension showed no signs of spheres or solid material settlement during storage in room temperature or at about 4 degree C. for at least one month.

Table 14 showed the effect of various doses of non-heat-treated or heat-treated spheres on thrombocytopenic rabbits

TABLE 14

Improvements in the Bleeding Time (BT) of rabbits treated with ultra-small spheres with no fibrinogen coating.

| Rabbit | Wt, kg | Plt Ct Pre | Plt Ct 0.5 hr post | Plt Ct 2.5 hr post | Plt Ct 24 hr post | BT 2 hr post | BT 24 hr post | HCT % |
|---|---|---|---|---|---|---|---|---|
| 24 | 2.5 | 41 | 22 | 19 | 20 | 177 | 250 | 23 |
| 25 | 2.7 | 38 | 4 | 8 | 3 | 385 | 685 | 28 |
| 26 | 2.6 | 46 | 21 | 3 | 10 | >900 | 533 | 23 |
| 27 | 2.5 | 33 | 22 | 10 | 5 | >900 | >900 | 24 |
| 28 | 2.8 | 22 | 9 | 11 | 9 | >900 | >900 | 30 |
| 29 | 2.7 | 40 | 40 | 45 | 38 | 415 | 260 | 28 |
| 30 | 2.9 | 32 | 50 | 68 | 79 | 315 | 325 | 21 |
| 31 | 2.7 | 23 | 26 | 19 | 14 | >900 | 404 | 29 |
| 32 | 2.8 | 32 | 27 | 16 | 14 | >900 | >900 | 33 |

Comments:

By comparison of rabbits infused with non-heat-treated spheres (number 24 to 29) it appeared that a dose of 4 mg sphere/kg was more efficacious than a dose of 1.33 mg/kg in that 2 out of 3 rabbits treated with the higher dose showed improvements as early as 2 hour post-infusion. By the 24$^{th}$ hour, all three rabbits treated with the higher dose (number 24, 25, 26) showed improvements while only 1 out of three treated with the lower dose (number 29) showed improvement. The difference between the results from the high vs low doses could not be explained on the basis of platelet counts because rabbit number 25 had a comparable platelet count with rabbit number 27 and 28, at both 2.5 and 24 hr post-infusion and yet showed better improvement in its BT at the corresponding time points.

Heat-treated spheres were still effective in improvement of the BT in thrombocytopenic rabbits (e.g. rabbit 30 and 31.) By comparison of the BT in rabbits treated with the heat-treated spheres with those treated with the non-heat-treated spheres (both infused with the same dose, 4 mg sphere/kg) it appears that heating for 10 hours at 60 degree C. might have diminished the activity of spheres somewhat. However, the number of rabbits used was insufficient to draw this conclusion and the effect of the excipient had not been excluded.

Although this experiment aimed at producing spheres using the novel Mid-link method, it was believed that by using a similar tubing system, all the other novel synthesis methods (i.e. without the addition of surfactant or detergent to the protein solution) namely, the Post-link, Pre-link, Bi-link and BiMid-link methods can all be used to produce spheres effective in improvement of bleeding volumes, bleeding episode and the severity of bleeding in thrombocytopenic animals including human.

In addition, the present invention envisions addition of other biological molecules that could affect a number of medical conditions. These molecules could be added before the addition of the desolvation agent, or after it, or co-mixed with the desolvation agent.

A partial list of such biological molecules would include any single or a combination of molecules such as: alkaloids, aminoacids and polypeptides, carbohydrates, carcinogens, globulin and immunoglobulin, halogenated compounds, hormones, lipids, nucleotides, porphyrins, steroids, vitamins, lectins, metal halide, oxide or sulfide, antibacterial compounds, antifungal compounds, antiviral compounds, enzymes. Of particular interest would be the inclusion of coagulation factors such as fibrinogen or von Willebrand factor; or chemotherapeutic agents including alkylating agents (e.g. nitrogen mustard, chlorambucil, cyclophosphamide, or busulfan), antimetabolites (e.g. methotrexate or its analogs, 6-mercaptopurine, cytosine arabinoside, 5-flourouracil), antibiotics (e.g. daunomycin, actinomycin-D or adriamycin), methylhydrazine, nitrosourea, hydroxyurea, imidazole carboxamide, procarbazine, mitotane, streptozotocin, 5-azacytidine and their analogs.

Other newer chemotherapeutic agents or adjuvants could also be included for encapsulation or binding to these sphere for targeting to cancer cells or slow release to decrease toxicity, including: thalidomide, dexamethasone, Bortezomib, melphalan, prednisone, lenalidomide, vincristine, clodronate, zoledronic acid, pamidronate, fludarabine, mitoxantrone, alemtuzumab, rituximab and their analogs.

Other important biological molecules such as interferon (all classes including interferon alpha, interferon beta and interferon gamma,) interleukins (all classes) and their antibodies (all classes) can likewise be captured or bound onto these spheres for increased efficacy, longer duration of action, lower side-effects, protection from degradation in vivo or targeting to in vivo sites.

Conclusion:

Spheres after heat treatment for 10 hours at 60 degree C. retained their efficacy in improving the Bleeding Time in thrombocytopenic rabbits.

A tubing system different from the prior art in its simplicity was capable of producing at least 559 ml of concentrated sphere suspension per minutes, before dilution with water and excipient for filling into bottles.

These spheres could remain in suspension for a prolong time (at least one month without settling to the bottom in the absence of shaking) and the suspension was stable without lyophilization. The sphere suspension could be infused into the patient directly intravenously. The spheres prepared in the prior art required lyophilization to preserve stability because the spheres were larger and would form a sediment at the bottom of the container unless shaken regularly. Lyophilized power needed reconstitution with a fluid which may not be available in critical situations such as under combat conditions or other disruptive situations. After reconstitution the larger spheres would settle unless those suspensions were regularly agitated or shaken. The sphere suspensions prepared by this Invention therefore have multiple practical advantages compared to those prepared by the disclosed prior art.

EXPERIMENT 15

Production of Ultra-small Spheres by a Novel BiMid-link Method

Purpose:

(1) To evaluate if spheres could be produced by a novel two step crosslinking method without the addition of surfactants or detergents in the protein solution, the first step comprising the mixing of a sub-stabilizing concentration of crosslinking agent with the protein solution, the second step involving the addition of a mixture containing a crosslinking agent at a stabilizing concentration which had been pre-mixed with the desolvating agent. (2) To evaluate the property of spheres formed by this BiMid-link method.

Rationale:

Experiment 5 and 7 had shown that by first mixing the protein solution for about 15 seconds with a sub-stabilizing concentration of crosslinking agent before the addition of the desolvation agent, the protein spheres obtained after the addition of the desolvation agent would be more uniform in size compared to the spheres formed by addition of the desolvation agent directly to the protein solution without using the sub-stabilizing concentration of crosslinking agent. Since the sub-stabilizing concentration of crosslinking agent was not able to hold spheres in the intact form upon dilution of the concentration of desolvation agent, a stabilizing concentration of crosslinking agent must be added after the formation of spheres to stabilize them against re-dissolving.

The present experiment is carried out to test if useful and highly uniform spheres could be formed by: (1) mixing a protein solution with a sub-stabilizing concentration of crosslinking agent for about 15 seconds, (2) then adding the desolvation agent which had been pre-mixed with a crosslinking agent such that upon mixing of this mixture of desolvation agent and crosslinking agent with the pre-treated protein solution, spheres could be formed that are both uniform and stable against re-dissolving, should the desolvation agent be removed or diluted later.

The advantage of using this BiMid-link method is that one fewer step which requires precise timing is needed compared to the Bi-link method. In the Bi-link method, at time zero the sub-stabilizing concentration of crosslinking agent is added; then at time 15 second (plus or minus 5 second) the desolvation agent is added; and then finally at another time point, the stabilizing concentration of crosslinking agent is added. This will require three mixing steps at three definite time-points. In a tubing set, such as described in the prior art (U.S. Pat. No. 6,013,285) three mixing points are needed and at least two respective post-mixing segments of exact lengths must be included to allow the respective time delays before the next ingredient is to be mixed in at the next mixing junction. With this new BiMid-link method, only two mixing junction points are needed.

This method is novel because the protein solution does not require addition of a detergent or surfactant to produce a sphere suspension that is monodisperse and without aggregates and without spheres larger than 5 micron.

The effect of binding a sub-stabilizing concentration of crosslinking agent on protein molecules still in solution is unknown in terms of the physiological properties of the spheres to be subsequently formed. The effect of adding the second dose of crosslinking agent together with the desolvation agent to irreversibly bind the partially-treated protein molecules from soluble form into a solid sphere is also unknown. Therefore this method is novel and the sphere suspension formed will need to be tested in thrombocytopenic rabbits.

This experiment will include spheres produced by an addition step of coating with fibrinogen in vitro as part of the manufacturing steps. Both the blank spheres without fibrinogen added in vitro and those with fibrinogen added in vitro will be evaluated.

Material and Methods:

Aliquots of a 25% solution of human serum albumin purchased from Baxter (Buminate) was diluted with water to achieve a 10% solution, without the addition of surfactant or a detergent. The sub-stabilizing concentration of crosslinking agent was prepared by dilution of the 25% glutaraldehyde (GL) solution purchased from Sigma (G6257) with water to an initial concentration of 0.15 mg per ml. The desolvation agent was ethanol diluted with water to 60% (vol per vol) premixed with GL at 0.5 mg/ml. Fibrinogen was dissolved to result in a solution with 0.4 mg fibrinogen per ml in a solution containing sodium tetradecyl sulphate (STS) at 1 mg per ml in water. The STS was used to facilitate the solubility of the fibrinogen molecules and not in any way designed to affect the formation of spheres or their stability after synthesis. The excipient of dextrose solution was prepared by dissolving 22 gram of dextrose (purchased from Sigma, D9434) in 100 ml of water.

A portion consisting of 2.1 ml of the 10% albumin solution was added to a 50-ml polypropylene tube at room temperature ranging from 20 to 24 deg C. At time zero, 1.05 ml of the sub-stabilizing concentration of GL was added to the tube and the mixture well mixed by shaking. At time point of 15 seconds, 31.5 ml of the desolvation agent (EG60 containing 0.5 mg GL per ml) was added. The contents were again quickly and well mixed. At time point 30 seconds (counting from time zero) 3.15 ml of the fibrinogen solution was added. Again the mixture was well shaken immediately. After 1 to 2 hours, 12.6 ml of a dextrose solution was added as excipient. This preparation was called Preparation 15-F.

For control, 3.15 ml of water was added in stead of the 3.15 ml of fibrinogen solution at the same time-point of 30 seconds after the addition of the sub-stabilizing concentration of GL (time zero). This control preparation was called Preparation 15-B.

Results:

Microscopic examination of both Preparation 15-F and 15-B showed that the spheres were about 0.1 micron in diameter and very uniform; without any aggregates and without any spheres larger than 1 micron. This means there were less than 10,000 large spheres present per milliliter volume of the suspension.

Evaluation of these sphere suspensions in thrombocytopenic rabbits showed that both were effective in reducing the Bleeding Time in these animals, as shown in Table 15.

TABLE 15

Platelet count and Bleeding Time at various time points in thrombocytopenic rabbits.

| Rabbit No | Weight Kg | Prep | Dose, mg/kg | Plt Ct, Pre | Plt Ct, 0.5 h Post | Plt Ct, 2.5 h Post | Plt Ct, 24 h Post | BT, 2 h Post | BT, 24 h Post | HCT % |
|---|---|---|---|---|---|---|---|---|---|---|
| 41 | 2.9 | 15-B | 4 | 48 | 19 | 49 | 39 | 155 | 157 | 25 |
| 42 | 2.8 | 15-B | 4 | 219 | 52 | 31 | 31 | 290 | 355 | 25 |
| 43 | 3 | 15-B | 4 | 40 | 16 | 33 | 16 | 155 | 265 | 24 |
| 44 | 2.6 | 15-B | 1.3 | 41 | 39 | 46 | 16 | 340 | 755 | 24 |
| 45 | 2.5 | 15-B | 1.3 | 47 | 22 | 48 | 44 | 330 | 255 | 21 |
| 46 | 2.9 | 15-B | 1.3 | 48 | 25 | 12 | 19 | >900 | 405 | 22 |
| 47 | 2.9 | 15-F | 4 | 33 | 41 | 19 | 40 | 735 | 240 | 24 |
| 48 | 2.6 | 15-F | 4 | 33 | 32 | 33 | 30 | 715 | 124 | 27 |
| 49 | 2.7 | 15-F | 4 | 15 | 20 | 39 | 44 | 375 | 225 | 25 |
| 50 | 2.9 | 15-F | 1.3 | 42 | 50 | 24 | 41 | >900 | >900 | 24 |
| 51 | 2.9 | 15-F | 1.3 | 23 | 27 | 46 | 42 | 745 | 200 | 25 |
| 52 | 2.8 | 15-F | 1.3 | 50 | 21 | 12 | 28 | 290 | 345 | 28 |

Comments:

The data indicated that 4 mg spheres/kg was more effective than 1.3 mg sphere/ml for both Preparation 15-B and 15-F. The limited number of rabbits in this experiment suggested that Preparation 15-B (no fibrinogen added in vitro during synthesis) may be more effective than Preparation 15-F (fibrinogen added in vitro during synthesis for comparison). However, whether this is true needed to be confirmed with larger number of animals.

Both preparations were injected into rabbits without first removing the alcohol from the preparation and seemed to cause no ill effect on the anesthesized rabbits during the performance of Bleeding Time (BT). However, this. Invention envisions the possibility of first removing the ethanol from the sphere preparation before injection into awake animals (such as in clinical practice) to diminish any confusion arising from the effect of alcohol. There are many methods available for the removal of alcohol, such as by reverse osmosis, or by diafiltration using various methods including hollow fiber filters such as those used in the wine industry to prepare low alcohol or no-alcohol drinks.

Conclusion:

The new BiMid-link method produced spheres which were very uniform and effective in the treatment of bleeding in thrombocytopenic rabbits whether they were coated in vitro during the synthesis step with fibrinogen or not.

EXPERIMENT 16

Production of the Biologic Device Using Bovine Serum Albumin

Purpose: To show that an albumin source other than human albumin can result in useful suspensions of spheres similar to those in function as human albumin spheres and to evaluate if added salt to the desolvation agent had any adverse effect.

Rationale: Human spheres without fibrinogen had an effect in reducing bleeding time in thrombocytopenic rabbits suggesting that rabbit fibrinogen can bind to human albumin spheres. This experiment evaluates if spheres made from bovine serum albumin can also bind rabbit fibrinogen in vivo to result in a similar beneficial medical effect.

It is expected that any animal source of albumin, when made under the conditions of this invention, can result in beneficial effects such as those obtained with human albumin spheres.

Material and Methods: Bovine albumin can be purchased from a variety of sources such as Sigma-Aldrich (St Louis, Mo.), Desert Biologicals (Phoenix, Ariz.), Boval (Cleburne, Tex.), BioPharm Laboratories (Alpine, Utah), Equitech-Bio, Inc (Kerrville, Tex.) and SeraCare Life Sciences (Milford, Mass.). A solution of Bovine Serum Albumin (BSA, 25%) was diluted with distilled water to result in 100 ml each of a 24%, 20% and 16% solution. A dilute glutaraldehyde solution was prepared by dilution of a 25% of glutaldehyde solution with distilled water to 0.15 mg of glutaraldehyde per ml. The desolvation agent was a solution containing 75% of ethyl alcohol in water, supplemented with 0.26 mg of sodium chloride per ml and 0.5 mg of glutaraldehyde per ml of solution.

At time Zero, 50 ml of the dilute glutaraldehyde was added to the 100 ml of 24% BSA at room temperature (20 to 23 degree C.) and immediately well mixed. At time equal to 15 seconds, 900 ml of the desolvation agent was added, resulting immediately in turbidity indicating that spheres were formed. Examination under the microscope showed essentially only of spheres about 0.5 micron (and smaller) in diameter without the presence of aggregates.

The procedure was repeated with similar volume to the 20% and 16% BSA solutions with similar results.

It is expected that infusion of these spheres made in the absence of added surfactants or added detergents and without the addition of fibrinogen during the synthesis steps can reduce the bleeding time in thrombocytopenic and thrombocytopathic patients.

It is also expected that a range of sodium chloride added to the desolvation agent, for example, from zero up to 0.9 mg per ml may have no adverse effect on the formation of spheres. A comparable range of added sodium chloride to the desolvation agent may also have a negligible effect when the other novel methods of synthesis (without added surfactant or detergents) as described in this invention are used.

Conclusion: In all previous experiments, the desolvation agent did not contain any added salt. This experiment showed that the inclusion of 0.26 mg of sodium chloride in the desolvation agent, using the "BiMid-link" approach did not adversely affect the formation of spheres resulting in a suspension without the presence of aggregates.

SUMMARY OF EXPERIMENTS

The above experiments disclosed several new methods of producing spheres and sphere suspensions that were effective in the treatment of bleeding in thrombocytopenic rabbits. The methods are new and unexpected because the protein solution does not require addition of surfactants or detergents to result in sphere suspensions containing no aggregations and without large spheres with diameter greater than 5 micron.

The spheres disclosed in these discoveries were novel because they were effective in vivo without the need of coating with a coagulation factor such as fibrinogen in the manufacturing steps. The spheres were also novel in that even after prolong storage they were able to bind fibrinogen and other coagulation factors from plasma without the involvement or addition of a crosslinking agent in the mixture containing the spheres and the plasma. In addition the spheres appear to be able to concentrate fibrinogen molecules on its surface or interior when mixed with plasma containing a reduced concentration of fibrinogen.

This disclosure here teaches a new method of treatment of thrombocytopenia with infusion of a suspension of protein devices which do not have any known biological molecules bound in vitro which would affect hemostasis, but which are capable of binding molecules in vivo from the plasma such that the combination of these devices with the endogenous molecules could reduce bleeding time and bleeding volume in thrombocytopenic animals. The etiology of low platelet count can be due to any medical or surgical or physiological reasons and they all potentially can be treated with these devices. It is expected that even animals which have anti-platelet antibodies (or alloimmunized in any other way) or having tendencies to bleed from any other reasons can be medically treated with these devices.

What is claimed is:

1. A method of treating a patient having a bleeding disorder with a protein nanoparticle suspension, said method comprising the steps of:
   a) preparing a protein nanoparticle suspension comprising the steps of:
      preparing a premixed solution by mixing a crosslinking agent with a desolvating agent, said crosslinking agent containing at least a glutaraldehyde solution, said desolvating agent containing ethyl alcohol; and
      adding said premixed solution to an albumin solution without a presence of an added surfactant or detergent, so that initiation of a crosslinking action by said crosslinking agent on protein molecules in said albumin solution start at a same time as that of said desolvating agent in forming spheres from said protein molecules; and
   b) administering a predetermined amount of said protein nanoparticle suspension to the patient having a bleeding disorder resulting in decreased bleeding by the administration of said protein nanoparticle suspension which in vitro has no biologically active molecules bound to said protein spheres; and c) binding at least one biologically active molecule in vivo to said protein spheres.

2. The method of treatment of a patient in accordance with claim 1, further comprising: the method of administration is by intravenous administration.

3. The method of treatment of a patient in accordance with claim 1, wherein said protein spheres are each less than five micron in any one dimension.

4. The method of treatment of a patient in accordance with claim 1, wherein said biologically active molecule in vivo is comprised of coagulation factors.

5. The method of treatment of a patient in accordance with claim 1, wherein the patient tends to bleed from either lack of sufficient concentration of platelets or from lack of sufficient platelet function.

6. The method of treatment of a patient in accordance with claim 1, wherein the patient suffers from a group illness selected from the group consisting of dilutional thrombocytopenia, cancer, cancer treatment, anti-platelet medication, anti-platelet medication overdose, and viral infection.

7. The method of treating a patient in accordance with claim 1, further comprising: a time of administration of said protein nanoparticle solution is prophylactic in anticipation of an occurrence of said bleeding disorder.

* * * * *